(12) United States Patent
Fuchiwaki et al.

(10) Patent No.: US 10,147,883 B2
(45) Date of Patent: Dec. 4, 2018

(54) MATERIAL FOR ORGANIC ELECTROLUMINESCENT DEVICE AND ORGANIC ELECTROLUMINESCENT DEVICE INCLUDING THE SAME

(71) Applicant: Samsung Display Co., Ltd., Yongin-si, Gyeonggi-do (KR)

(72) Inventors: Junta Fuchiwaki, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 161 days.

(21) Appl. No.: 15/077,682

(22) Filed: Mar. 22, 2016

(65) Prior Publication Data
US 2017/0033289 A1   Feb. 2, 2017

(30) Foreign Application Priority Data

Jul. 28, 2015   (JP) .................................. 2015-148426

(51) Int. Cl.
*B32B 19/00*   (2006.01)
*H01L 51/00*   (2006.01)
(Continued)

(52) U.S. Cl.
CPC .......... *H01L 51/006* (2013.01); *C07C 211/54* (2013.01); *C07C 211/58* (2013.01);
(Continued)

(58) Field of Classification Search
CPC ............... H01L 51/006; H01L 51/0059; H01L 51/5056; H01L 51/0052; H01L 51/0058;
(Continued)

(56) References Cited

U.S. PATENT DOCUMENTS

2011/0073852 A1* 3/2011 Yokoyama ........... C07D 471/04
257/40

FOREIGN PATENT DOCUMENTS

| JP | 2002-241352 A | 8/2002 |
| JP | 2003-238501 A | 8/2003 |
| WO | WO 2009/139475 A1 | 11/2009 |

OTHER PUBLICATIONS

Zhu et al. (Chem. Commun., 2012, 48, 2695-2697).*

* cited by examiner

*Primary Examiner* — Shane Fang
(74) *Attorney, Agent, or Firm* — Lewis Roca Rothgerber Christie LLP

(57) ABSTRACT

A material for an organic electroluminescent device, represented by Formula 1, and an organic electroluminescent device including the same. The material for an organic electroluminescent device according to an embodiment of the present disclosure may be a triamine derivative in which the nitrogen atoms are connected (e.g., coupled) via the meta ring positions of $L_1$ and $L_2$ linkers, which may be represented by Formula 2.

Formula 1

(Continued)

-continued
Formula 2
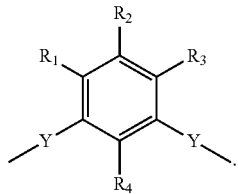
(2)
13 Claims, 2 Drawing Sheets
(51) Int. Cl.
    *C07C 211/54*     (2006.01)
    *C07C 211/58*     (2006.01)
    *H01L 51/50*     (2006.01)
(52) U.S. Cl.
    CPC ...... H01L 51/0059 (2013.01); *H01L 51/0052* (2013.01); *H01L 51/0058* (2013.01); *H01L 51/5012* (2013.01); *H01L 51/5056* (2013.01)
(58) Field of Classification Search
    CPC .. H01L 51/0012; C07C 211/54; C07C 211/58
    See application file for complete search history.

MATERIAL FOR ORGANIC ELECTROLUMINESCENT DEVICE AND ORGANIC ELECTROLUMINESCENT DEVICE INCLUDING THE SAME

CROSS-REFERENCE TO RELATED APPLICATIONS

This application claims priority to and the benefit of Japanese Patent Application No. 2015-148426, filed on Jul. 28, 2015, the entire content of which is incorporated herein by reference.

BACKGROUND

One or more aspects of example embodiments of the present disclosure are related to a material for an organic electroluminescent device and an organic electroluminescent device including the same. Aspects of the present disclosure are related to a hole transport material for an organic electroluminescent device with high emission efficiency and a long lifetime, and an organic electroluminescent device including the same.

Organic electroluminescent (EL) displays have been actively developed in recent years. Unlike liquid crystal displays (LCDs) and the like, organic EL displays are so-called self-emitting type (e.g., "self-emitting" or "self-luminescent") displays, in which holes and electrons are respectively injected from an anode and a cathode into an emission layer, where they recombine and cause light emission by a luminescent material (including an organic compound) included in the emission layer, thereby displaying images.

An example organic EL device may include an anode, a hole transport layer on the anode, an emission layer on the hole transport layer, an electron transport layer on the emission layer, and a cathode on the electron transport layer. Holes from the anode may be injected via the hole transport layer into the emission layer. Electrons from the cathode may be injected via the electron transport layer into the emission layer. The holes and the electrons injected into the emission layer may recombine to generate excitons in the emission layer. The organic EL device emits light using energy generated by radiation deactivation (e.g., radiative decay) of the excitons. The organic EL device is not limited to the aforementioned configuration, and many modifications thereof are possible.

Display applications require organic EL devices having high efficiencies and long lifetimes. Organic EL devices in the blue light emission region require high driving voltages, and may therefore suffer from low emission efficiencies compared to organic EL devices in the green and red light emission regions. Ongoing strategies for achieving organic EL devices with high efficiencies include normalization, stabilization, and increasing the durability of a hole transport layer.

Various aromatic amine compounds have been used as hole transport materials in the hole transport layers of organic EL devices in the related art. However, further improvements in the emission efficiency of a device are desired. A diamine derivative has been suggested as a favorable material for increasing the emission efficiency of an organic EL device in the blue light emission region. A triamine derivative having three amine moieties has also been suggested in the related art. However, because the ionization potential of each of these compounds is too low, and the energy gap of each of these compounds is too small, organic EL devices in the related art that use these compounds may still be affected by limitations including the loss of recombined excitons, etc. For example, when a hole transport layer containing the triamine derivative is adjacent to an emission layer, the efficiency of the device may still be deteriorated due to transfer of excited energy (e.g., excitons) from the emission layer. Accordingly, an organic EL device having even higher efficiency is required.

SUMMARY

One or more aspects of example embodiments of the present disclosure are directed toward a material for an organic EL device having high emission efficiency and an organic EL device including the same.

One or more example embodiments of the present disclosure provide a material for an organic EL device having high emission efficiency in the blue light emission region, and an organic EL device including the same in at least one layer.

One or more example embodiments of the present disclosure provide a material for an organic EL device represented by Formula 1:

Formula 1

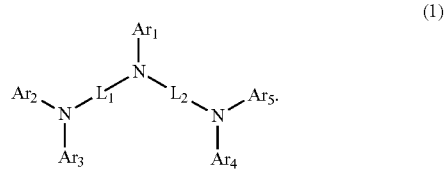

In Formula 1, $Ar_1$ to $Ar_5$ may each independently be selected from a substituted or unsubstituted aryl group having 6 to 30 carbon atoms for forming a ring and a substituted or unsubstituted heteroaryl group having 4 to 30 carbon atoms for forming a ring, and $L_1$ and $L_2$ may each independently be a linker represented by Formula 2:

Formula 2

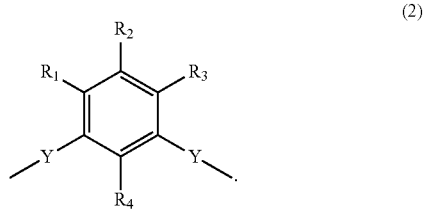

In Formula 2, Y may be selected from a direct linkage and a substituted or unsubstituted arylene group having 6 to 30 carbon atoms for forming a ring, and $R_1$ to $R_4$ may each independently be selected from hydrogen, deuterium, a halogen atom, a hydroxyl group, a cyano group, a nitro group, an alkoxy group, an aryloxy group, an alkyl or aryl substituted silyl group, an alkyl or aryl substituted boryl group, a substituted or unsubstituted alkyl group, a substituted or unsubstituted aryl group, and a substituted or unsubstituted heteroaryl group.

The material for an organic EL device may include three amine moieties and may exhibit high hole mobility. The $L_1$ and $L_2$ aromatic linkers may connect (e.g., couple) the amines at meta ring positions, and the highest occupied molecular orbital (HOMO) energy level of the material may be relatively close to that of the emission layer. When the excited state singlet energy level is high, the transition (e.g., diffusion or loss) of singlet state excited energy (e.g., excitons) from the emission layer may be restrained or reduced, and the emission efficiency of an organic EL device may be increased or improved. Further, the charge transport properties of the layer using the derivative compound may be improved, and the lifetime of the organic EL device may be increased or improved.

In some embodiments, $L_1$ and/or $L_2$ may each independently be an arylene group selected from Formulae (3) to (14):

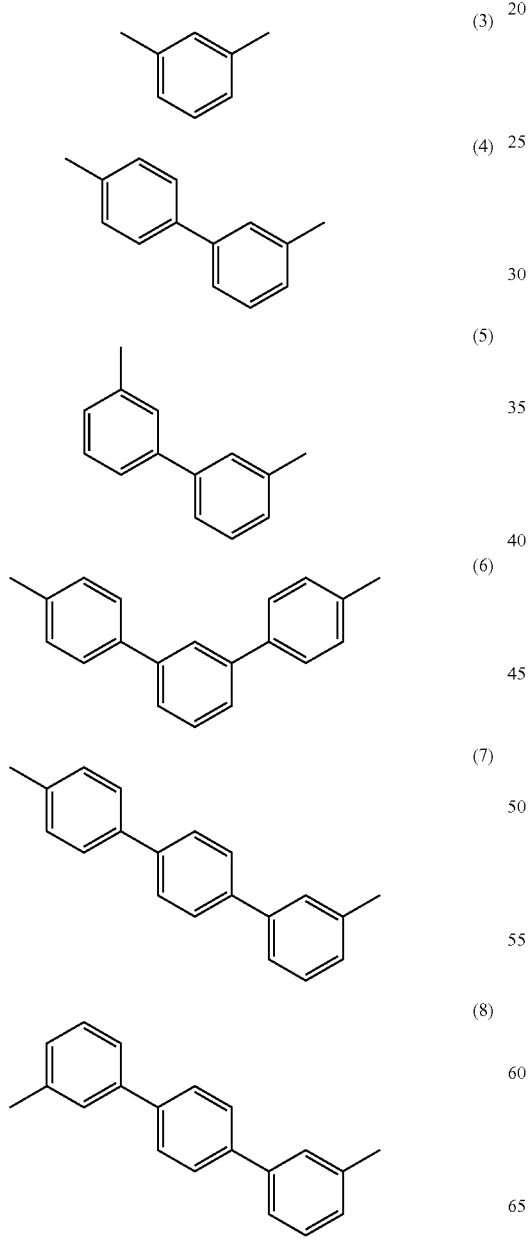

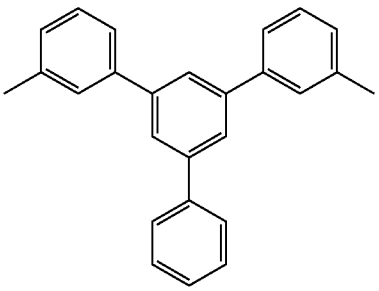

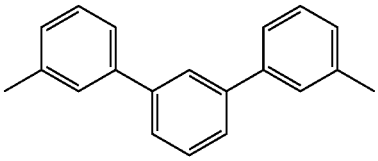

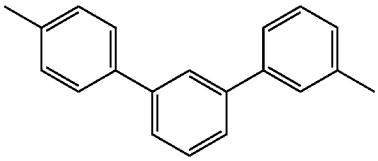

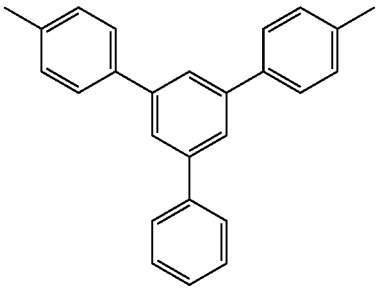

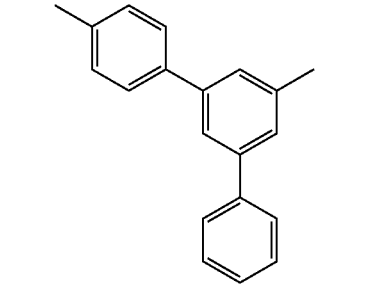

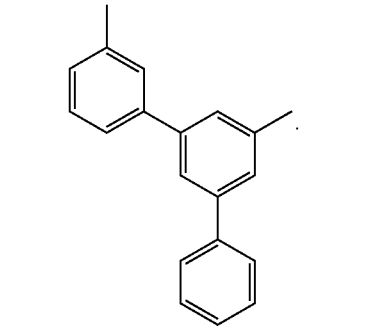

The material for an organic EL device according to an embodiment of the present disclosure may improve the efficiency of the organic EL device.

In some embodiments, $L_1$ and/or $L_2$ may each independently be an arylene group selected from Formulae (15) to (17):

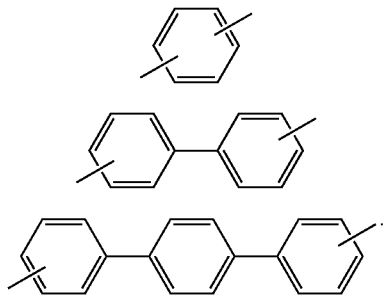

(15)

(16)

(17)

The material for an organic EL device according to an embodiment of the present disclosure may improve the high efficiency of the organic EL device.

In some embodiments, $Ar_1$ to $Ar_5$ may each independently be a substituted or unsubstituted aryl group selected from Formulae (18) to (26):

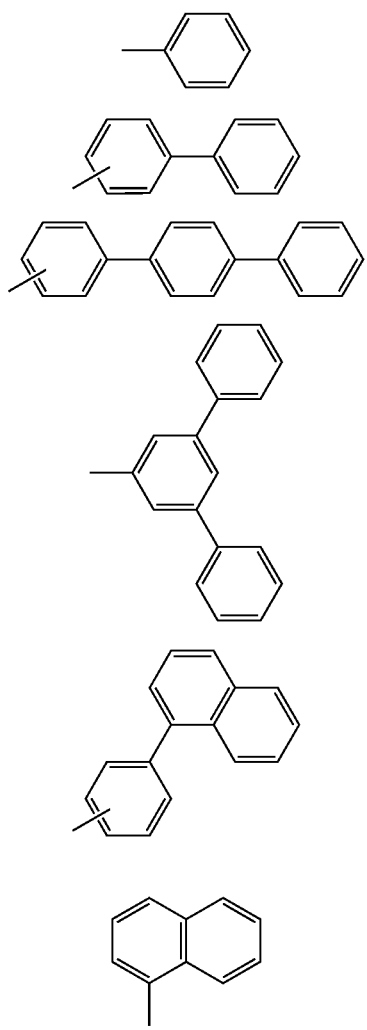

(18)

(19)

(20)

(21)

(22)

(23)

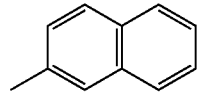

(24)

(25)

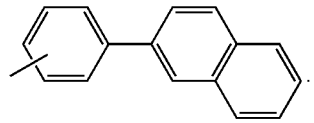

(26)

The material for an organic EL device according to an embodiment of the present disclosure may improve the efficiency of the organic EL device.

In some embodiments, $R_1$ to $R_4$ may each independently be at least one selected from hydrogen, deuterium, a phenyl group, a methyl group, fluorine, and a cyano group.

The material for an organic EL device according to an embodiment of the present disclosure may improve the efficiency of the organic EL device.

In some embodiments, $L_1$ and/or $L_2$ may each independently be an arylene group selected from Formulae (27) to (29):

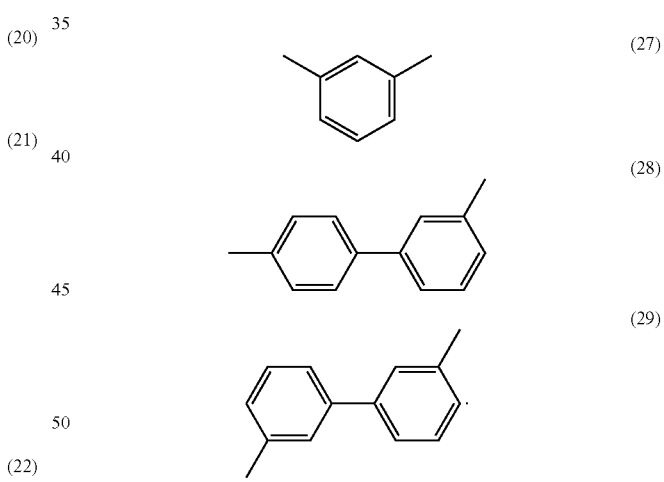

(27)

(28)

(29)

The material for an organic EL device according to an embodiment of the present disclosure may improve the efficiency of the organic EL device.

In one embodiment, the material for an organic EL device may have a molecular weight of about 500 g/mol to about 1,000 g/mol.

The material for an organic EL device according to an embodiment of the present disclosure may improve the efficiency of the organic EL device.

In one embodiment, the material for an organic EL device may be at least one triamine derivative selected from Formulae (30) to (43):

(30)
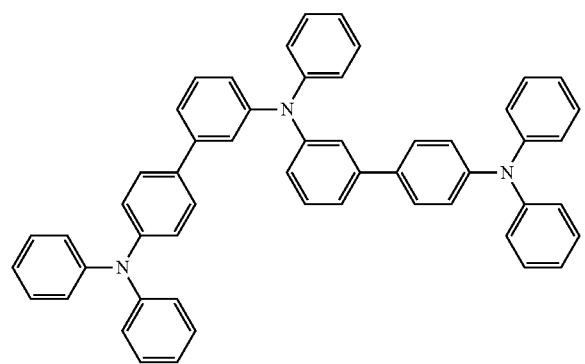
(31)
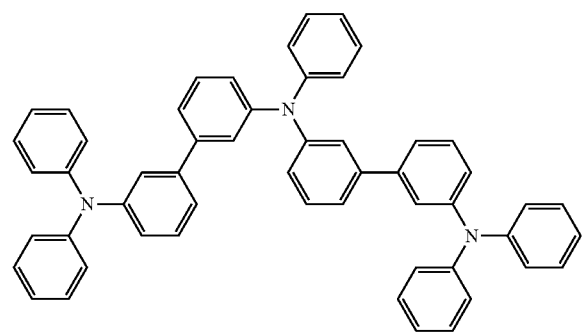
(32)
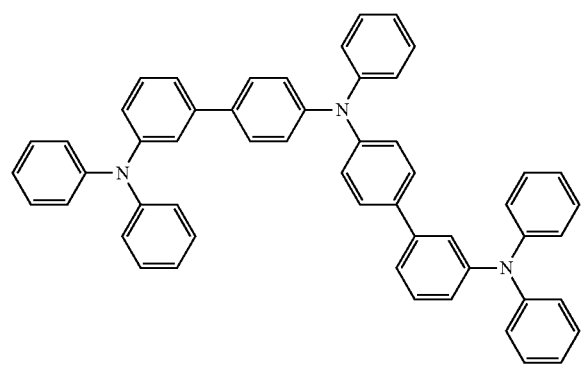
(33)
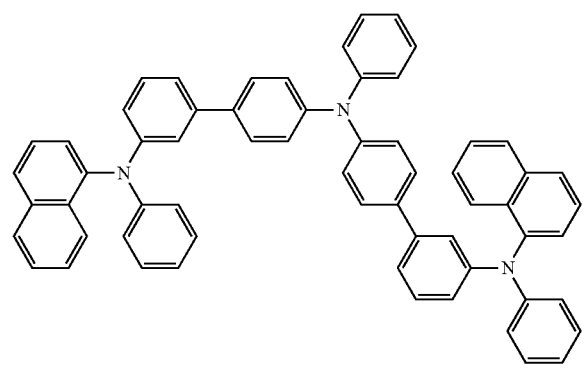
(34)
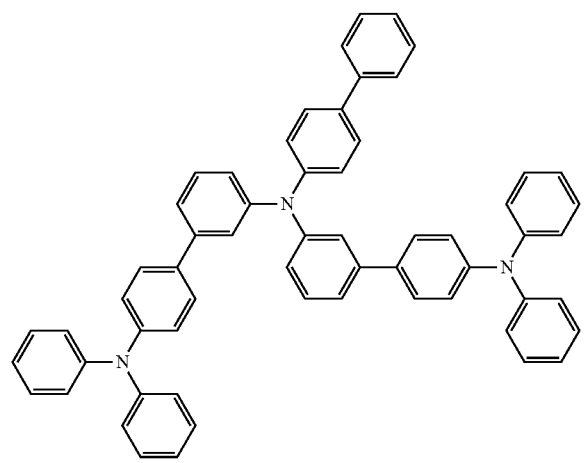
(35)
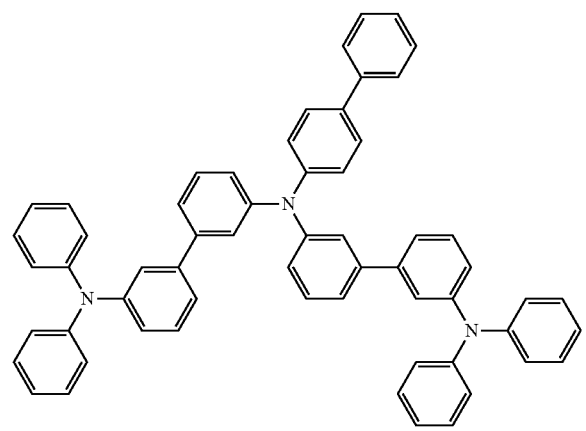

(36)
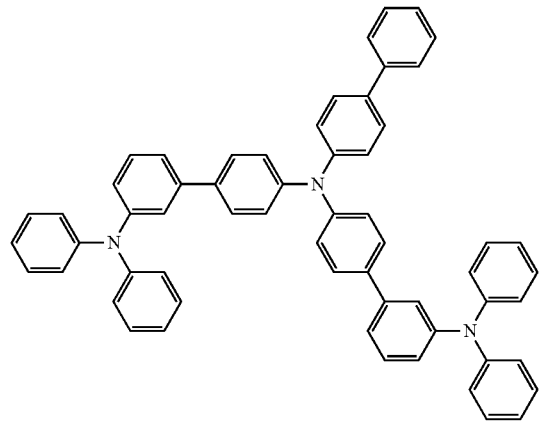
(37)
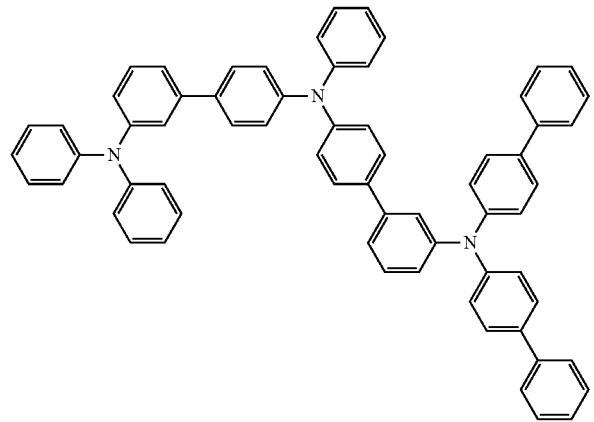
(38)
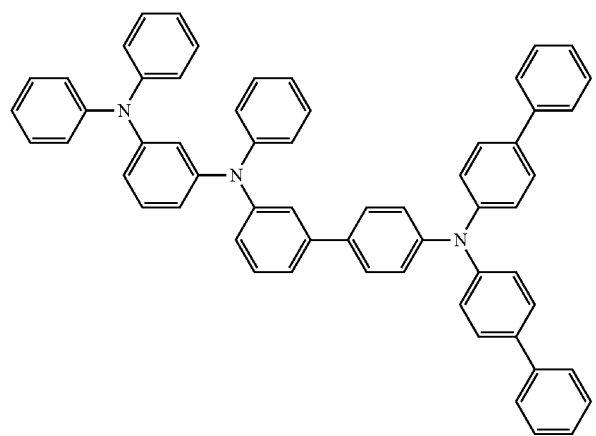
(39)
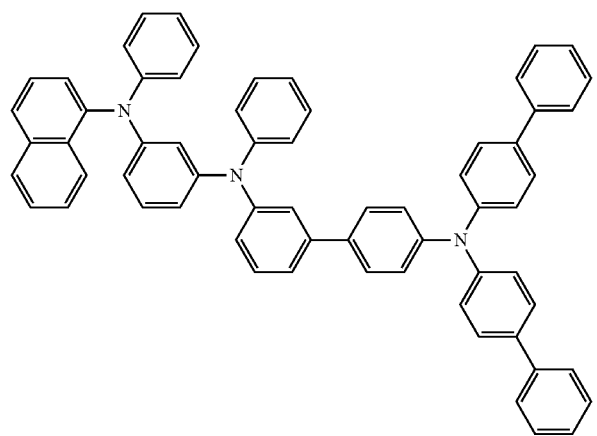
(40)
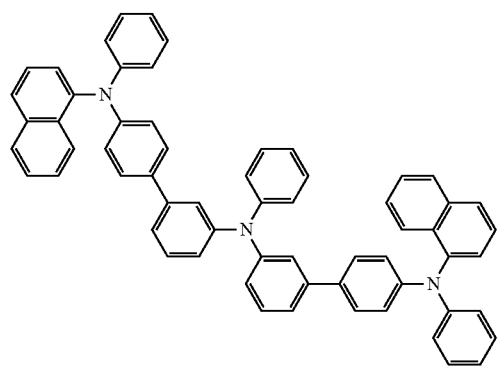
(41)
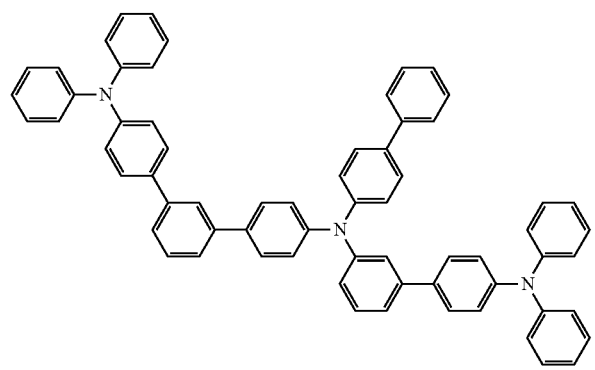

-continued (42)

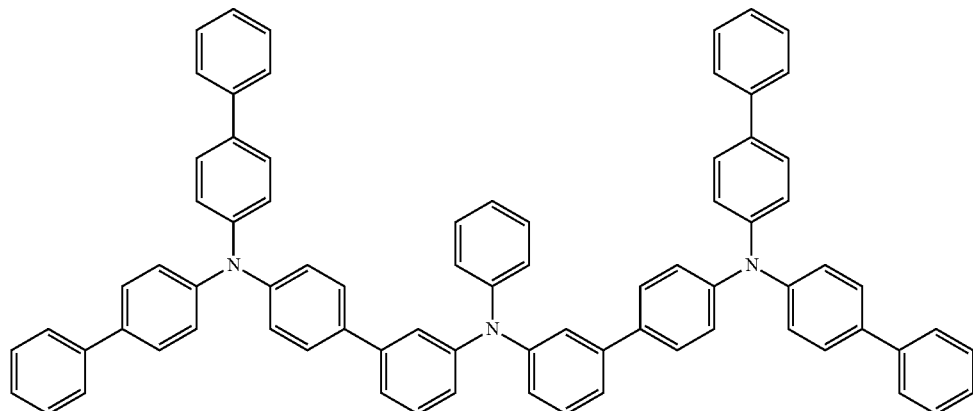

(43)

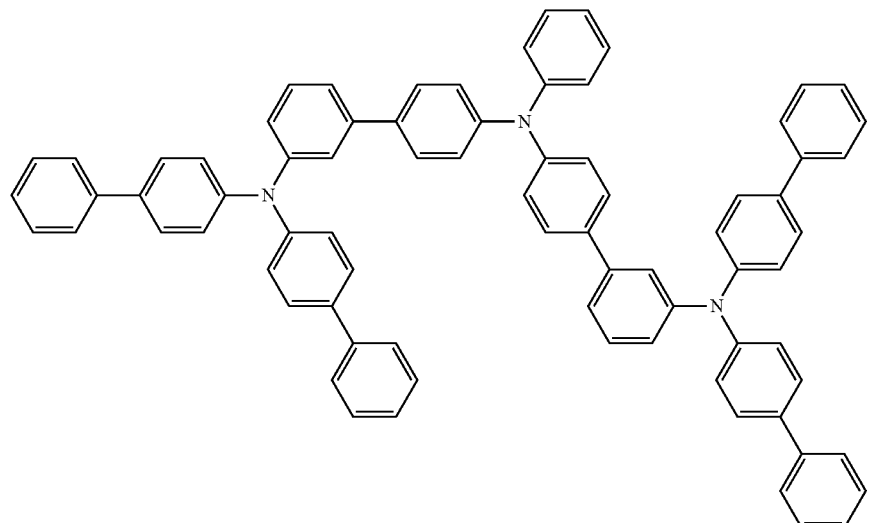

The material for an organic EL device according to an embodiment of the present disclosure may improve the efficiency of the organic EL device.

One or more embodiments of the present disclosure provide an organic EL device including the material for an organic EL device in at least one layer.

An organic EL device may include an anode, a cathode facing the anode, and a plurality of organic layers between the anode and the cathode, wherein at least one selected from the plurality of organic layers includes a material for an organic EL device represented by Formula 1:

Formula 1

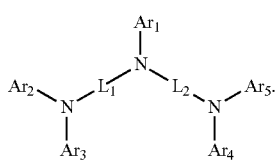

(1)

In Formula 1, $Ar_1$ to $Ar_5$ may each independently be selected from a substituted or unsubstituted aryl group having 6 to 30 carbon atoms for forming a ring and a substituted or unsubstituted heteroaryl group having 4 to 30 carbon atoms for forming a ring, and $L_1$ and $L_2$ may each independently be a linker represented by Formula 2:

Formula 2

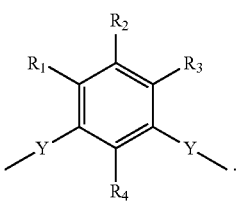

(2)

In Formula 2, Y may be selected from a direct linkage and a substituted or unsubstituted arylene group having 6 to 30 carbon atoms for forming a ring, and $R_1$ to $R_4$ may each independently be selected from hydrogen, deuterium, a halogen atom, a hydroxyl group, a cyano group, a nitro group, an alkoxy group, an aryloxy group, an alkyl or aryl substituted silyl group, an alkyl or aryl substituted boryl group, a substituted or unsubstituted alkyl group, a substituted or unsubstituted aryl group, and a substituted or unsubstituted heteroaryl group.

In one embodiment, the plurality of organic layers may include a hole injection layer, a hole transport layer, and an emission layer, and the material for an organic EL device may be included in at least one layer selected from the hole injection layer, the hole transport layer, and the emission layer.

The organic EL device according to an embodiment of the present disclosure may achieve high emission efficiency when one of the materials for an organic EL device is included in at least one layer.

In one embodiment, one of the materials for an organic EL device may be included in at least one laminated layer between an emission layer and an anode in the organic EL device.

In one embodiment, one of the materials for an organic EL device may be included in a layer adjacent to the emission layer of the organic EL device.

The organic EL device according to an embodiment of the present disclosure may achieve high emission efficiency when one of the materials for an organic EL device is included in at least one of the laminated layers between the emission layer and the anode.

The organic EL device according to an embodiment of the present disclosure may achieve high emission efficiency when one of the materials for an organic EL device is included in a layer adjacent to the emission layer.

BRIEF DESCRIPTION OF THE DRAWINGS

The accompanying drawings are included to enable further understanding of the present disclosure, and are incorporated in and constitute a part of this specification. The drawings illustrate example embodiments of the present disclosure and, together with the description, serve to explain principles of the present disclosure.

In the drawings.

DETAILED DESCRIPTION

Figure 1:
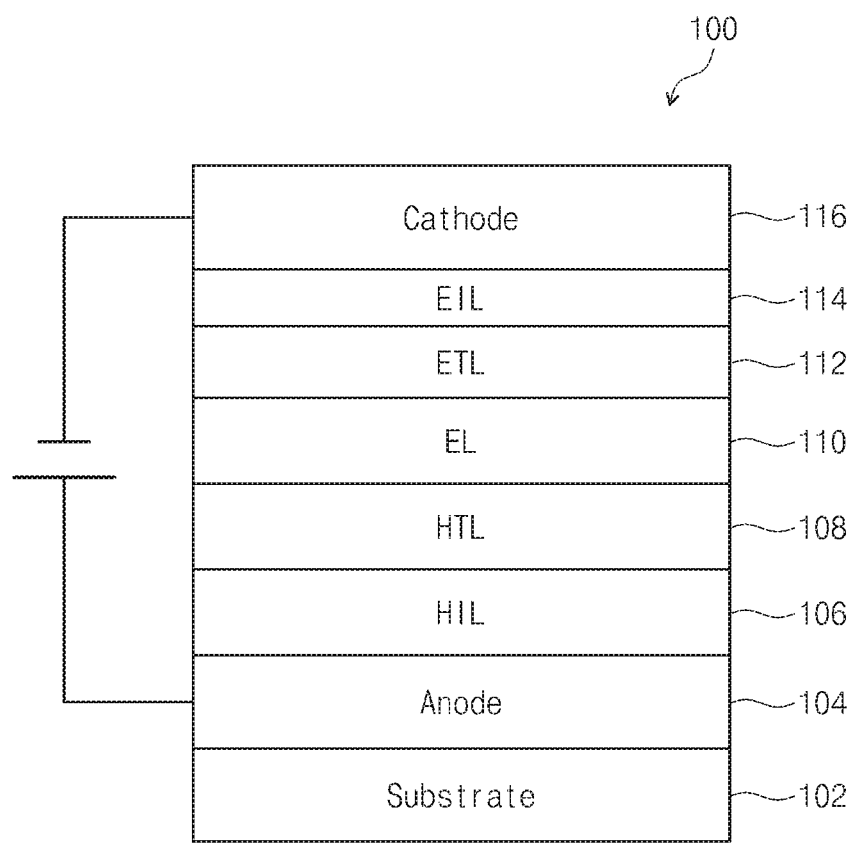
FIG. 1 is a schematic diagram illustrating an organic EL device 100 according to an embodiment of the present disclosure.

The singlet excited state energy level of a hole transport material may be suitably lowered when a triamine derivative is used instead of a diamine derivative, and the triamine derivative has a molecular structure in which the nitrogen atom of the central amine is connected (e.g., coupled) with the two nitrogen atoms of the outer amines via the meta ring positions of two independent linking arylene groups. Therefore, the charge transport properties of the layer using the triamine derivative may be improved, and the efficiency of the organic EL device may be improved or increased.

Hereinafter, the material for an organic EL device according to an embodiment of the present disclosure and the organic EL device including the same will be described in more detail with reference to the accompanying drawings. The material for an organic EL device according to an embodiment of the present disclosure and the organic EL device including the same may, however, be embodied in different forms and should not be construed as being limited to the embodiments set forth herein. In the drawings, like reference numerals refer to like elements or elements having like functions throughout, and repeated explanation thereof will not be provided.

In the drawings, the thicknesses of layers, films, panels, regions, etc., may be exaggerated for clarity. It will be understood that when an element such as a layer, film, region, or substrate is referred to as being "on" another element, it can be directly on the other element or intervening element(s) may also be present. In contrast, when an element is referred to as being "directly on" another element, no intervening elements are present.

The material for an organic EL device according to an embodiment of the present disclosure may be an amine compound represented by Formula 1:

Formula 1

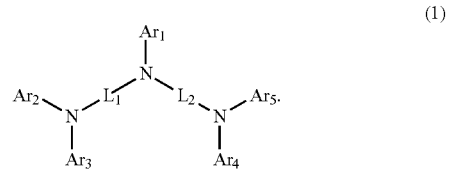

(1)

In Formula 1, $Ar_1$ to $Ar_5$ may each independently be selected from a substituted or unsubstituted aryl group having 6 to 30 carbon atoms for forming a ring and a substituted or unsubstituted heteroaryl group having 4 to 30 carbon atoms for forming a ring. As used herein, "atoms for forming a ring" may refer to "ring-forming atoms". $L_1$ and $L_2$ may each independently be a linker represented by Formula 2:

Formula 2

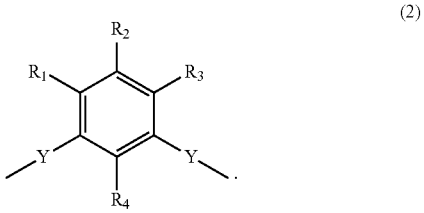

(2)

In Formula 2, Y may be selected from a direct linkage and a substituted or unsubstituted arylene group having 6 to 30 carbon atoms for forming a ring, and $R_1$ to $R_4$ may each independently be selected from hydrogen, deuterium, a halogen atom, a hydroxyl group, a cyano group, a nitro group, an alkoxy group, an aryloxy group, an alkyl or aryl substituted silyl group, an alkyl or aryl substituted boryl group, a substituted or unsubstituted alkyl group, a substituted or unsubstituted aryl group, and a substituted or unsubstituted heteroaryl group. As used herein, "direct linkage" may refer to a bond such as a single bond.

As described above, $L_1$ and/or $L_2$ in Formula 1 may each independently be a linker represented by Formula 2, and in Formula 2, Y may be selected from a direct linkage and a substituted or unsubstituted arylene group having 6 to 30 carbon atoms for forming a ring. Non-limiting examples of the arylene group having 6 to 30 carbon atoms for forming a ring used as Y may include a phenylene group, a naphthalene group, an anthracenylene group, a phenanthrylene group, a biphenylene group, a terphenylene group, a quaterphenylene group, a fluorenylene group, a triphenylene group, a pyrenylene group, a benzofluoranthenylene group, a chrysenylene group, and a group obtained by connecting two or more thereof.

Non-limiting examples of the substituent of Y may include a halogen atom, a hydroxyl group, a cyano group, a nitro group, an alkoxy group, an aryloxy group, an alkyl or aryl substituted silyl group, an alkyl or aryl substituted boryl group, a substituted or unsubstituted alkyl group, a substituted or unsubstituted aryl group, and a substituted or unsubstituted heteroaryl group.

$R_1$ to $R_4$ may each independently be selected from hydrogen, deuterium, a halogen atom, a hydroxyl group, a cyano group, a nitro group, an alkoxy group, an aryloxy group, an alkyl or aryl substituted silyl group, an alkyl or aryl substituted boryl group, a substituted or unsubstituted alkyl group, a substituted or unsubstituted aryl group, a substituted or unsubstituted heteroaryl group, etc. Non-limiting examples of $R_1$ to $R_4$ may include hydrogen, a phenyl group, a biphenyl group, a methyl group, fluorine, a cyano group, etc. In some embodiments, $R_1$ to $R_4$ may each independently be selected from hydrogen, a phenyl group, a methyl group, and fluorine.

$L_1$ and $L_2$ may each independently be selected from a meta-phenylene group, a 2,3'-biphenylene group, a 3,3'-biphenylene group, a 3,4'-biphenylene group, a terphenylene group, and a quaterphenylene group. In some embodiments, $L_1$ and $L_2$ may be selected from a meta-phenylene group and a 2,3'-biphenylene group.

In Formula 1, non-limiting examples of the aryl group having 6 to 30 carbon atoms for forming a ring may include a phenyl group, a naphthyl group, an anthracenyl group, a phenanthryl group, a biphenyl group, a terphenyl group, a quaterphenyl group, a fluorenyl group, a triphenylene group, a biphenylene group, a pyrenyl group, a benzofluoranthenyl group, a glyceryl group, a phenylnaphthyl group, a naphthylphenyl group, etc. In some embodiments, the aryl group having 6 to 30 carbon atoms for forming a ring used as $Ar_1$ to $Ar_5$ may be selected from a phenyl group, a biphenyl group, and a naphthyl group.

Non-limiting examples of the heteroaryl group having 4 to 30 carbon atoms for forming a ring used as $Ar_1$ to $Ar_5$ may include a pyridyl group, a quinolinyl group, a quinoxalinyl group, a phenanthrolinyl group, a pyrrolyl group, an indolyl group, a carbazolyl group, a benzimidazolyl group, an oxazolyl group, an oxadiazolyl group, a triazolyl group, a furanyl group, a benzofuranyl group, a dibenzofuranyl group, a thiophenyl group, a benzothiophenyl group, a dibenzothiophenyl group, a silole group, a benzosilole group, a dibenzosilole group, etc.

In some embodiments, $Ar_1$ to $Ar_5$ may each be substituted with one selected from an alkyl group having 1 to 6 carbons, an alkoxy group having 1 to 6 carbon atoms, and a phenyl group having 1 to 24 carbon atoms. Non-limiting examples of the alkyl group having 1 to 6 carbon atoms may include a methyl group, an ethyl group, an n-propyl group, an i-propyl group, an n-butyl group, an s-butyl group, a t-butyl group, an n-pentyl group, an n-hexyl group, a c-propyl group, a c-butyl group, a c-pentyl group, a c-hexyl group, etc. Non-limiting examples of the alkoxy group having 1 to 6 carbon atoms may include a methoxy group, an ethoxy group, an n-propoxy group, an i-propoxy group, an n-butoxy group, an s-butoxy group, a t-butoxy group, an n-pentoxy group, an n-hexoxy group, a c-propoxy group, a c-butoxy group, a c-pentoxy group, a c-hexoxy group, etc.

The molecular weight of the material for an organic EL device according to an embodiment of the present disclosure may be about 500 g/mol to about 1,000 g/mol. If the molecular weight is less than about 500 g/mol, the glass transition temperature may be low, and the organic EL device may be unstable. If the molecular weight is greater than about 1,000 g/mol, the formation of an organic EL device using an evaporation method may not be suitable or appropriate.

When the material for an organic EL device according to an embodiment of the present disclosure has three amine moieties, the hole mobility of the material may be high. In addition, when the nitrogen atoms of the three amine moieties are connected (e.g., coupled) via the meta ring positions of $L_1$ and $L_2$, the HOMO energy level of the material may be relatively close to that of the emission layer. Accordingly, the transition (e.g., diffusion or loss) of singlet state excited energy (e.g., excitons) from the emission layer may be restrained or reduced, and the emission efficiency of an organic EL device may be increased or improved. Further, the charge transport properties of the layer using the triamine derivative may be improved, and the lifetime of the organic EL device may be increased or improved. For example, the HOMO energy level of the material for an organic EL device may be close to the HOMO energy level of the emission layer, and the emission efficiency of the organic EL device may be improved.

The material for an organic EL device according to an embodiment of the present disclosure may be at least one triamine derivative selected from Formulae (30) to (43):

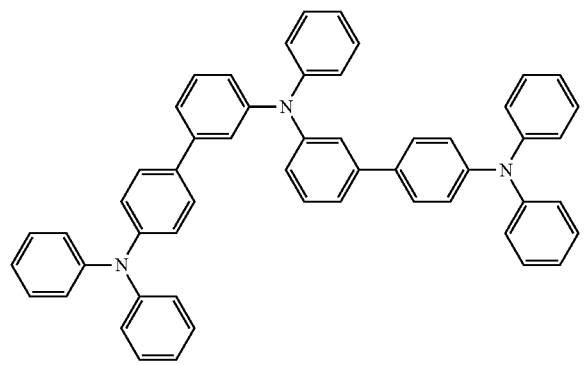

(30)

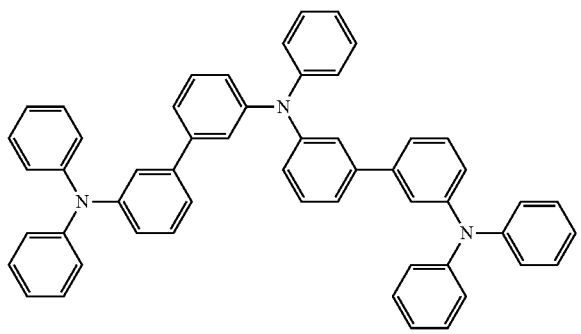

(31)

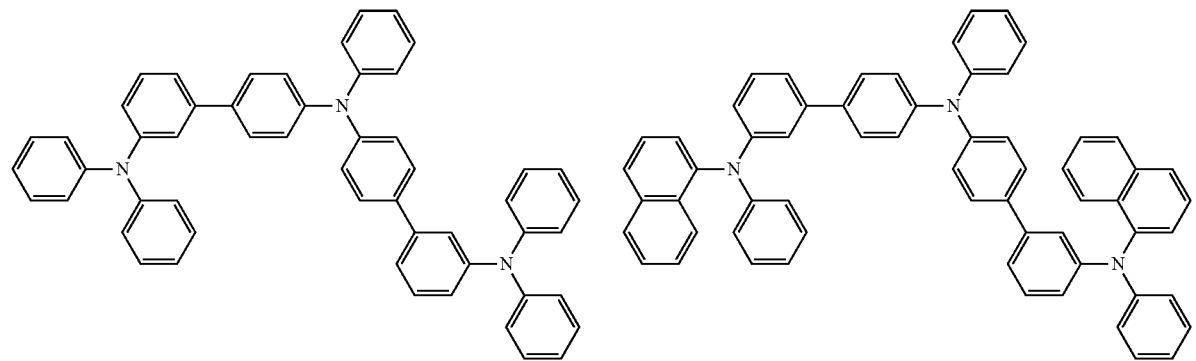
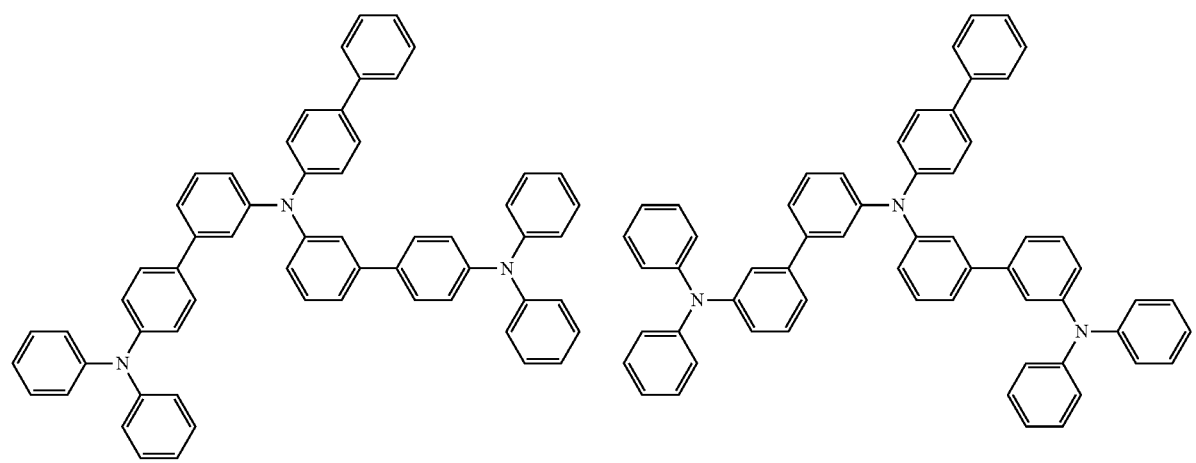
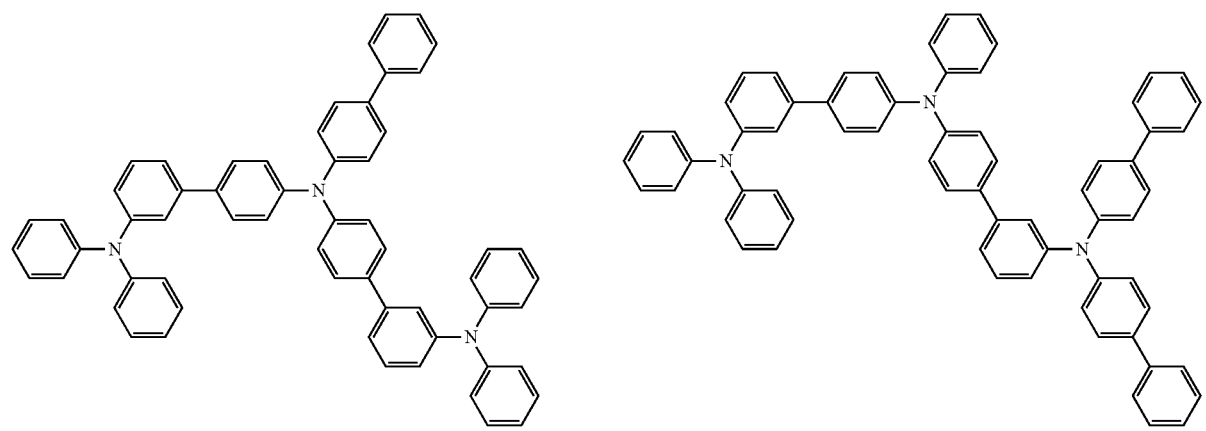

(38)
(39)
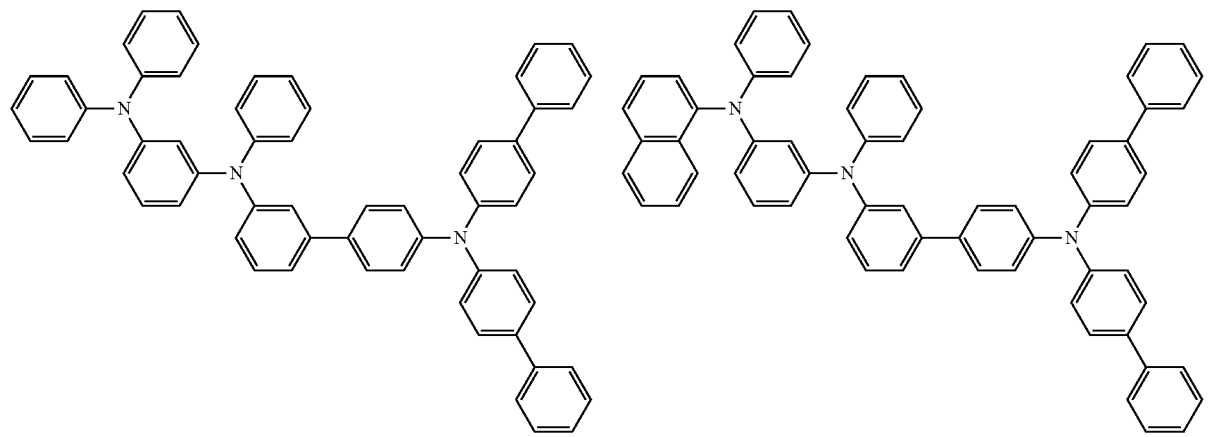
(40)
(41)
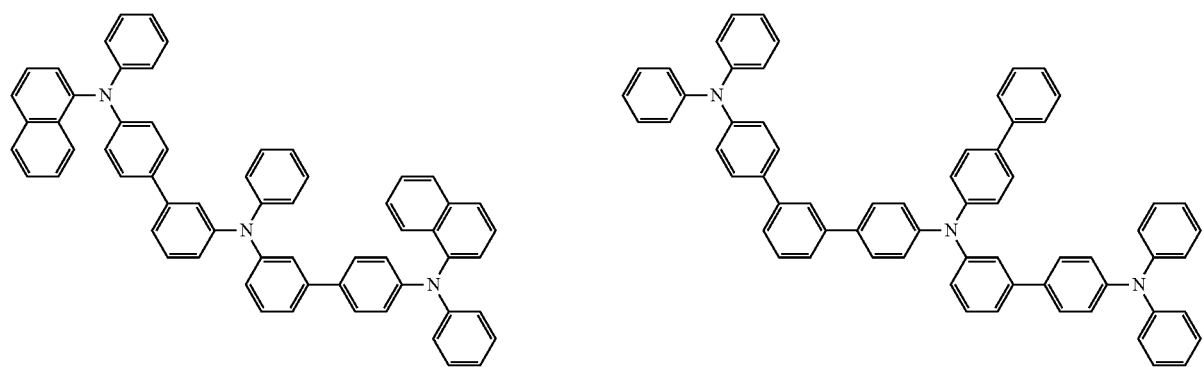
(42)
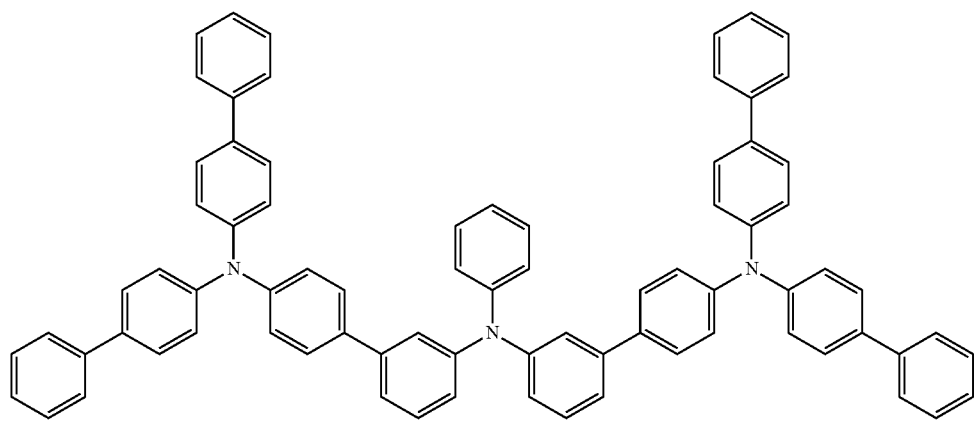

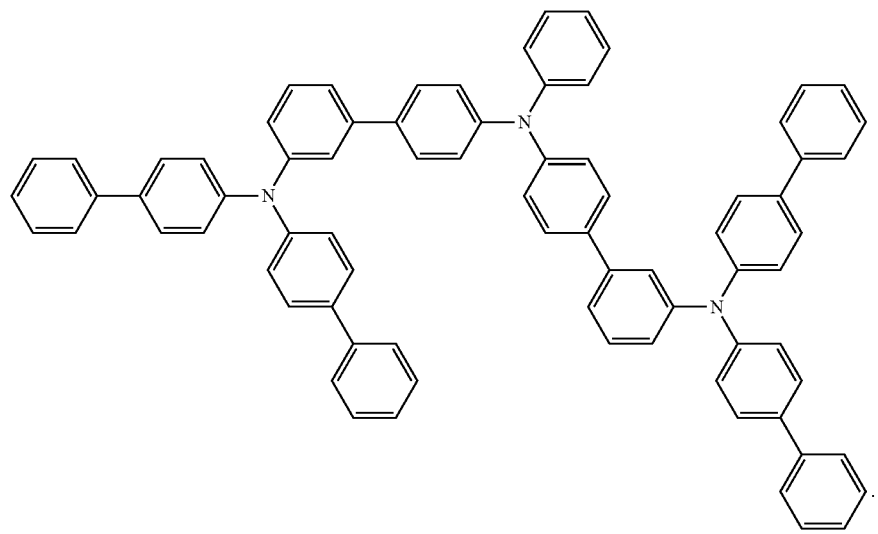

The material for an organic EL device according to an embodiment of the present disclosure may be included in at least one layer selected from a plurality of organic layers constituting the organic EL device. For example, the material may be included in at least one layer selected from the laminated layers between the emission layer and the anode of the organic EL device.

As described above, when the material for an organic EL device according to an embodiment of the present disclosure has three amine moieties, the hole mobility of the material may be high. In addition, when the nitrogen atoms of the three amine moieties are connected (e.g., coupled) via the meta ring positions of $L_1$ and $L_2$, the HOMO energy level of the material may be relatively close to that of the emission layer, and the singlet excited state energy level may be high. Accordingly, the transition (e.g., diffusion or loss) of excited energy (e.g., excitons) from the emission layer may be restrained or reduced, and the emission efficiency of the organic EL device may be increased or improved. Further, the charge transport properties of the layer using the triamine derivative may be improved, and the lifetime of the organic EL device may be increased or improved.

Since the material for an organic EL device according to an embodiment of the present disclosure has three amine moieties, the hole mobility of the material may be high, particularly in a layer adjacent to an emission layer. In addition, when the nitrogen atoms of the three amine moieties are connected (e.g., coupled) via the meta ring positions of $L_1$ and $L_2$, the HOMO energy level of the material may be relatively close to that of the emission layer, and the singlet excited state energy level may be high. Accordingly, the transition (e.g., diffusion or loss) of excited energy (e.g., excitons) from the emission layer may be restrained or reduced, and the emission efficiency of the organic EL device may be increased or improved. Further, the charge transport properties of the layer using the triamine derivative may be improved, and the lifetime of the organic EL device may be increased or improved.

Organic EL Device

An organic EL device including a material for an organic EL device according to an embodiment of the present disclosure will be explained in more detail. FIG. 1 is a schematic diagram illustrating an organic EL device 100 according to an embodiment of the present disclosure. The organic EL device 100 may include, for example, a substrate 102, an anode 104, a hole injection layer 106, a hole transport layer 108, an emission layer 110, an electron transport layer 112, an electron injection layer 114, and a cathode 116. In one embodiment, the material for an organic EL device according to an embodiment of the present disclosure may be used in at least one laminated layer between the emission layer and the anode.

Here, a case where the material for an organic EL device according to an embodiment of the present disclosure is used in the hole transport layer 108 will be explained. However, embodiments of the present disclosure are not limited thereto.

The substrate 102 may be a transparent glass substrate, a semiconductor substrate formed using silicon, a flexible substrate of a resin, etc.

The anode 104 may be on the substrate 102 and may be formed using indium tin oxide (ITO), indium zinc oxide (IZO), etc.

The hole injection layer (HIL) 106 may be formed on the anode 104 using a suitable material available in the related art to a thickness of about 10 nm to about 150 nm. Non-limiting examples of such material may include triphenylamine-containing poly ether ketone (TPAPEK), 4-isopropyl-4'-methyldiphenyliodoniumtetrakis (pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), 4,4',4"-tris{N,N-diphenylamino}triphenylamine (TDATA), 4,4',4"-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate (PEDOT/PSS), polyaniline/camphor sulfonic acid (PANI/CSA), polyaniline/poly(4-styrenesulfonate (PANI/PSS), etc.

The hole transport layer (HTL) 108 may be formed on the hole injection layer 106 using the material for an organic EL device according to an embodiment of the present disclosure to a thickness of about 10 nm to about 150 nm.

In some embodiments, when the material for an organic EL device according to an embodiment of the present disclosure is used as the host material of the emission layer (EL) 110, the hole transport layer 108 may be formed using a suitable hole transport material available in the related art. Non-limiting examples of such hole transport material may include 1,1-bis[(di-4-tolylamino)phenyl]cyclohexane (TAPC), a carbazole derivative (such as N-phenyl carbazole and/or polyvinyl carbazole), N,N'-bis(3-methylphenyl)-N, N'-diphenyl-[1,1-biphenyl]-4,4'-diamine (TPD), 4,4',4''-tris (N-carbazolyl)triphenylamine (TCTA), N,N'-di(1-naphthyl)-N,N'-diphenylbenzidine (NPB), etc. In some embodiments, the hole transport layer 108 may be formed by combining the hole transport material of the related art with the material for an organic EL device according to an embodiment of the present disclosure.

The emission layer (EL) 110 may be formed on the hole transport layer 108 using a suitable host material available in the related art to a thickness of about 10 nm to about 60 nm. Non-limiting examples of such host material for the emission layer 110 may include tris(8-quinolinolato)aluminum (Alq3), 4,4'-N,N'-dicarbazole-biphenyl (CBP), poly(N-vinylcarbazole) (PVK), 9,10-di(naphthalene-2-yl)anthracene (ADN), 4,4',4''-tris(N-carbazolyl)triphenylamine (TCTA), 1,3,5-tris(N-phenylbenzimidazole-2-yl)benzene (TPBI), 3-ted-butyl-9,10-di(naphtho-2-yl)anthracene (TBADN), distyrylarylene (DSA), 4,4'-bis(9-carbazole)-2,2'-dimethyl-biphenyl (dmCBP), etc.

The emission layer 110 may include a dopant material. Non-limiting examples of such material may include styryl derivatives (such as 1,4-bis[2-(3-N-ethylcarbazolyl)vinyl] benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalene-2-yl)vinyl) phenyl)-N-phenylbenzeneamine (N-BDAVBI)), perylene and derivatives thereof (such as 2,5,8,11-tetra-t-butylp-erylene (TBPe)), pyrene and derivatives thereof (such as 1,1-dipyrene, 1,4-dipyrenylbenzene, 1,4-bis(N,N-diphenylamino)pyrene), etc.

The electron transport layer (ETL) 112 may be formed on the emission layer 110 to a thickness of about 15 nm to about 50 nm using tris(8-hydroxyquinolinato)aluminum (Alq3) and/or a material having a nitrogen-containing aromatic ring (for example, a material including a pyridine ring (such as 1,3,5-tri[(3-pyridyl)-phen-3-yl]benzene), a material including a triazine ring (such as 2,4,6-tris(3'-(pyridine-3-yl)bi-phenyl-3-yl)1,3,5-triazine), and a material including an imidazole derivative (such as 2-(4-N-phenylbenzoimidazolyl-1-ylphenyl)-9,10-dinaphthylanthracene)).

The electron injection layer (EIL) 114 may be formed on the electron transport layer 112 to a thickness of about 0.3 nm to about 9 nm using a material including, for example, lithium fluoride (LiF), lithium-8-quinolinato (LiQ), etc.

The cathode 116 may be on the electron injection layer 114 and may be formed using a metal (such as aluminum (Al), silver (Ag), lithium (Li), magnesium (Mg) and/or calcium (Ca)), and/or a transparent material (such as ITO and/or IZO).

Each electrode and each layer constituting the organic EL device according to an embodiment of the present disclosure as described above may be formed using an appropriate or suitable layer forming method according to the material to be used (such as a vacuum evaporation method, a sputtering method, various coating methods, etc.)

In the organic EL device 100 according to an embodiment of the present disclosure, a hole transport layer capable of achieving high efficiency of the organic EL device may be formed using the material for an organic EL device according to an embodiment of the present disclosure.

In the organic EL device 100 according to an embodiment of the present disclosure, the material for an organic EL device according to an embodiment of the present disclosure may be used as a material of the hole injection layer and/or as a host material in the emission layer. As described above, an organic EL device with high efficiency may be manufactured when the material for an organic EL device according to an embodiment of the present disclosure is included in at least one layer selected from a plurality of organic layers constituting the organic EL device.

In some embodiments, the material for an organic EL device according to an embodiment of the present disclosure may also be applied in an active matrix type (e.g., active matrix) organic EL device using a thin-film transistor (TFT).

Manufacturing Method

The material for an organic EL device according to the present disclosure may be synthesized, for example, as follows.

Synthesis of Compound 30

Under an argon (Ar) atmosphere, 5.3 g of triphenylamine-4-boronic acid, 3 g of N,N-bis-(3-bromophenyl)aniline, 225 mL of toluene, 4.9 g of potassium phosphate, 0.93 g of tetrakis(triphenylphosphine)palladium(0), 18 mL of ethanol, and 30 mL of water were added to a 500 mL, three-necked flask, followed by heating and refluxing at about 90° C. for about 10 hours. The solid thus obtained was separated by flash column chromatography to obtain 4.8 g (Yield 75%) of Compound 31 as a white solid. The molecular weight of the target product when measured by FAB-MS was 731, the chemical structure was estimated as $C_{54}H_{41}N_3$, and the target product was identified as Compound 30.

Formula 9

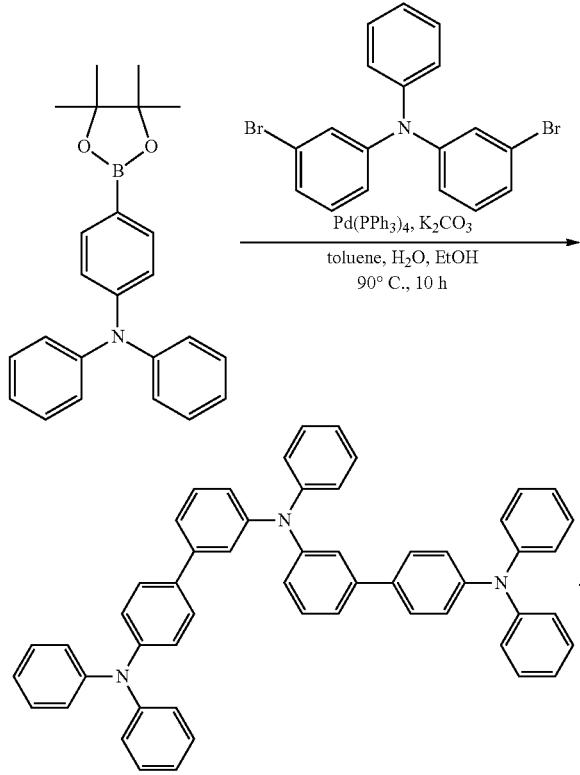

Compound 30
Synthesis of Compound 32

Under an Ar atmosphere, 5.3 g of triphenylamine-3-boronic acid, 3 g of N,N-bis-(3-bromophenyl)aniline, 225 mL of toluene, 4.9 g of potassium phosphate, 0.93 g of tetrakis(triphenylphosphine)palladium(0), 18 mL of ethanol, and 30 mL of water were added to a 500 mL, three-necked flask, followed by heating and refluxing at about 90° C. for about 10 hours. The solid thus obtained was separated by flash column chromatography to obtain 5.3 g (Yield 83%) of Compound 32 as a white solid. The molecular weight of the target product when measured by FAB-MS was 731, the chemical structure was estimated as $C_{54}H_{41}N_3$, and the target product was identified as Compound 32.

Formula 10

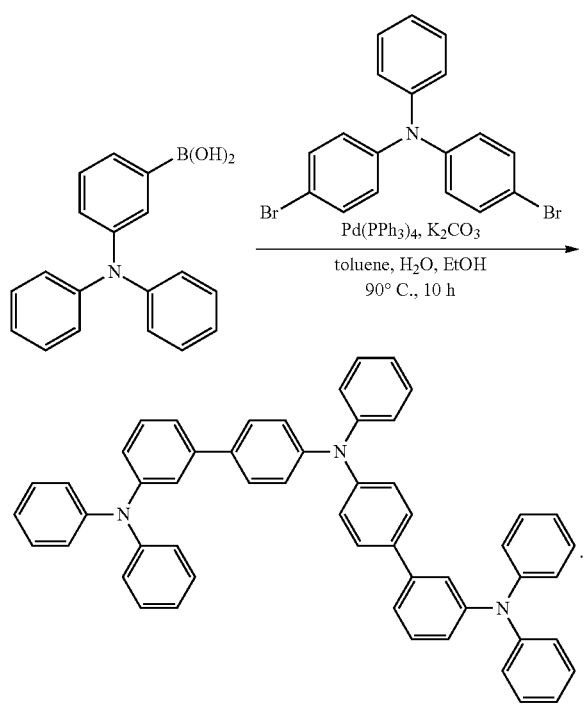

Compound 32

Organic EL devices according to Examples 1 and 2 were manufactured using Compound 30 and Compound 32 as hole transport materials, as produced by the above-described manufacturing methods.

In addition, organic EL devices of Comparative Examples 1 and 2 were manufactured using Comparative Compounds C-1 and C-2 as hole transport materials:

Comparative Compound C-1

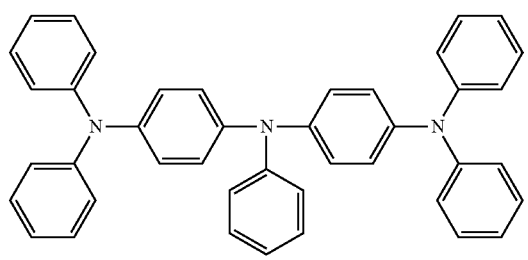

Comparative Compound C-2

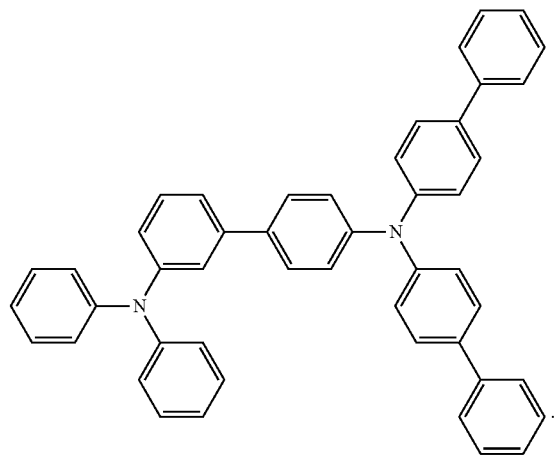

Figure 2:
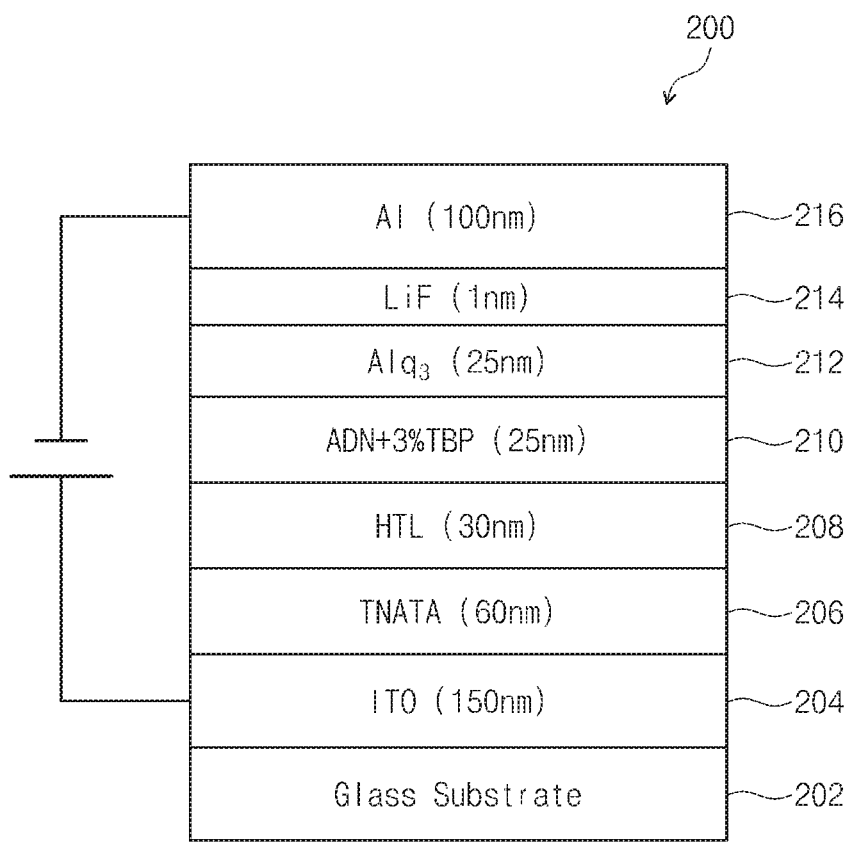
FIG. 2 is a schematic diagram illustrating an organic EL device 200 according to an embodiment of the present disclosure.

An organic EL device 200 according to an embodiment of the present disclosure is shown in FIG. 2. In this embodiment, a transparent glass substrate was used as a substrate 202, an anode 204 was formed using ITO to a layer thickness of about 150 nm, a hole injection layer 206 was formed using 2-TNATA to a layer thickness of about 60 nm, a hole transport layer 208 was formed to a layer thickness of about 30 nm, an emission layer 210 was formed using ADN doped with 3% TBP to a layer thickness of about 25 nm, an electron transport layer 212 was formed using Alq3 to a layer thickness of about 25 nm, an electron injection layer 214 was formed using LiF to a layer thickness of about 1 nm, and a cathode 216 was formed using Al to a layer thickness of about 100 nm.

The emission efficiency of each organic EL device 200 thus manufactured was evaluated at a current density of about 10 mA/cm². The evaluation results are shown in Table 1. For the evaluation of the emission properties of the organic EL devices thus manufactured, a C9920-11 Brightness Light Distribution Characteristics Measurement System by HAMAMATSU Photonics Co. was used.

TABLE 1

| Device manufacturing example | HTL compound | Current density (mA/cm²) | Driving voltage (V) | Emission efficiency (cd/A) | Lifetime LT50 (h) |
| --- | --- | --- | --- | --- | --- |
| Example 1 | Compound 30 | 10 | 7.1 | 6.9 | 1,900 |
| Example 2 | Compound 32 | 10 | 7.2 | 5.7 | 1,700 |
| Comparative Example 1 | Comparative Compound C-1 | 10 | 7.5 | 3.2 | 800 |
| Comparative Example 2 | Comparative Compound C-2 | 10 | 8.1 | 3.2 | 1,600 |

Referring to the results in Table 1, the organic EL devices of Examples 1 and 2 were recognized to have higher emission efficiencies when compared to those Comparative Examples 1 and 2. Since the material for an organic EL device according to an embodiment of the present disclosure has three amine moieties, hole mobility in the organic EL devices of Examples 1 and 2 may be high. In addition, because the nitrogen atoms of the three amine moieties are connected (e.g., coupled) via the meta ring positions of $L_1$ and $L_2$, the HOMO energy level of those materials may be relatively close to the HOMO energy level of the emission layer. When the singlet excited state energy level is high, the transition (e.g., diffusion or loss) of excited energy (e.g., excitons) from the emission layer may be restrained or reduced, thereby improving (e.g., increasing) the emission efficiency of the organic EL device. In addition, the charge transport properties of the layer using the triamine derivative may be improved, and the lifetime of the organic EL device may be further increased or improved. In Comparative Example 1, two amines are combined (e.g., coupled) via the para positions of an aryl linker, and the HOMO energy level may be higher than that of the emission layer. Accordingly, in Comparative Example 1, the hole transport layer 208 may collect holes, the emission efficiency may be deteriorated, reactivity may increase, and the lifetime of the organic EL device may decrease. In Comparative Example 2, a diamine was used, the charge transport properties of the layer may be deteriorated, and the emission efficiency of the organic EL device may be decreased.

From the results in Table 1, it may be recognized that high efficiency may be obtained when the material for an organic EL device according to an embodiment of the present disclosure is used as a hole transport material, compared to when the comparative compounds are used. The triamine derivative (which is the material for an organic EL device according to an embodiment of the present disclosure) has three amine moieties, and the hole mobility of the material may be high. In addition, since the nitrogen atoms of the three amine moieties are combined (e.g., coupled) via the meta ring positions of $L_1$ and $L_2$, the HOMO energy level of the material may be relatively close to that of the emission layer. In addition, the excited state singlet energy level may be high, the transition (e.g., diffusion or loss) of excited energy (e.g., excitons) from the emission layer may be restrained or reduced, and the emission efficiency of the organic EL device may be increased or improved. In addition, the charge transport properties may be improved, and the lifetime of an organic EL device may be further increased.

When the material for an organic EL device according to an embodiment of the present disclosure has three amine moieties, the hole mobility of the material may be high. In addition, since the nitrogen atoms of the three amine moieties are combined (e.g., coupled) via the meta ring positions of $L_1$ and $L_2$, the HOMO energy level of the material may be relatively close to that of the emission layer. In addition, the singlet excited state energy level may be high, the transition (e.g., diffusion or loss) of excited energy (e.g., excitons) from the emission layer may be restrained or reduced, and the emission efficiency of the organic EL device may be increased or improved. In addition, the charge transport properties may be improved, and the lifetime of an organic EL device may be further increased. Since the material for an organic EL device according to an embodiment of the present disclosure has a wide energy gap, application to the red and green light emitting regions may also be possible. For example, the HOMO energy level of the material for an organic EL device may be close to the HOMO energy level of the emission layer, and the emission efficiency of the organic EL device may be improved.

A material for an organic EL device achieving high emission efficiency, and an organic EL device including the same are provided by the present disclosure. When the material for an organic EL device according to an embodiment of the present disclosure is used in a hole transport layer adjacent to an emission layer, hole mobility may be high due to the inclusion of three amine moieties, the HOMO energy level may be relatively close to that of the emission layer because the nitrogen atoms of the amines are connected (e.g., coupled) via the meta ring positions of $L_1$ and $L_2$, and the transition (e.g., diffusion or loss) of excited energy (e.g., excitons) from the emission layer may be restrained or reduced, thereby improving the emission efficiency of an organic EL device. In addition, the charge transport properties may be improved, and the lifetime of the organic EL device may be increased. In some embodiments, remarkable effects may be obtained in the blue light emission region.

As used herein, expressions such as "at least one of", "one of", "at least one selected from", and "one selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The above-disclosed subject matter is to be considered illustrative and not restrictive, and the appended claims are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A material for an organic electroluminescent (EL) device represented by Formula 1:

Formula 1

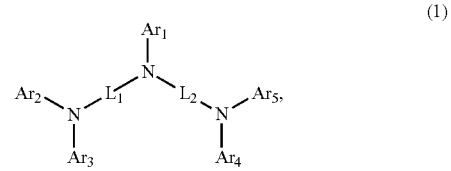

(1)

wherein in Formula 1, Formula 1 represents a triamine compound, and wherein Ar₁ to Ar₅ are each independently selected from a substituted or unsubstituted aryl group having 6 to 30 carbon atoms for forming a ring and a substituted or unsubstituted heteroaryl group having 4 to 30 carbon atoms for forming a ring, and L₁ and L₂ are each independently a linker represented by Formula 2:

Formula 2

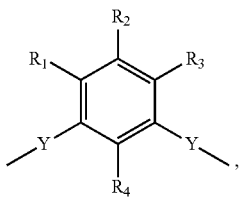
(2)

wherein Y is selected from a direct linkage and a substituted or unsubstituted arylene group having 6 to 30 carbon atoms for forming a ring, and R₁ to R₄ are each independently selected from hydrogen, deuterium, a halogen atom, a hydroxyl group, a cyano group, a nitro group, an alkoxy group, an aryloxy group, an alkyl or aryl substituted silyl group, an alkyl or aryl substituted boryl group, a substituted or unsubstituted alkyl group, a substituted or unsubstituted aryl group, and a substituted or unsubstituted heteroaryl group.

2. The material for an organic EL device of claim 1, wherein L₁ and/or L₂ are each independently an arylene group selected from Formulae (3) to (14):

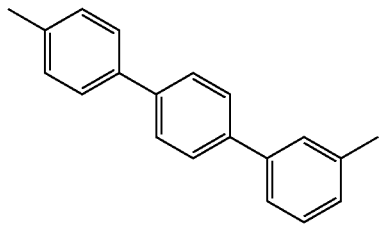
(7)

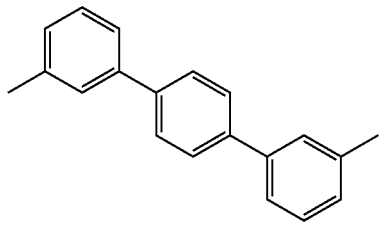
(8)

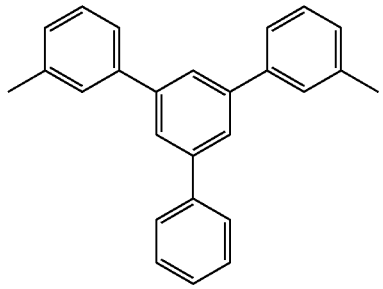
(9)

(3)

(4)

(5)

(6)

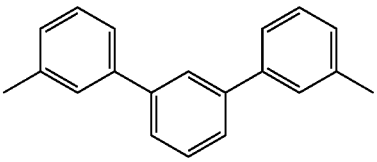
(10)

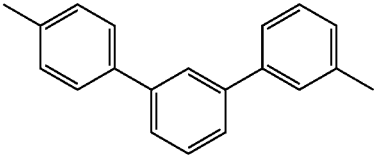
(11)

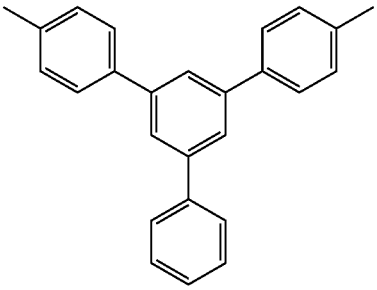
(12)

-continued

(13)
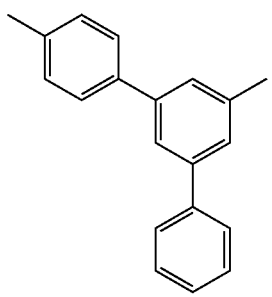

(14)
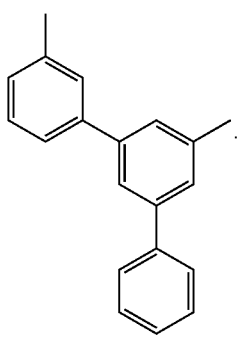

3. The material for an organic EL device of claim 1, wherein $L_1$ and/or $L_2$ are each independently an arylene group selected from Formulae (16) to (17):

(16)
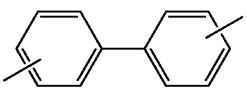

(17)
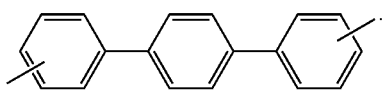

4. The material for an organic EL device of claim 1, wherein $Ar_1$ to $Ar_5$ are each independently a substituted or unsubstituted aryl group selected from Formulae (18) to (26):

(18)
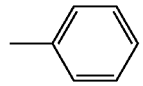

(19)
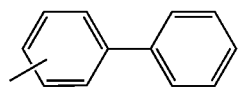

(20)
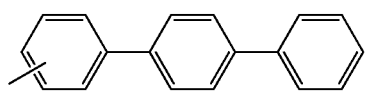

-continued

(21)
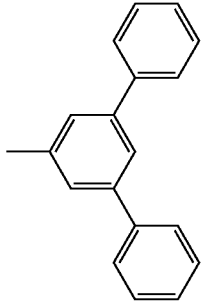

(22)
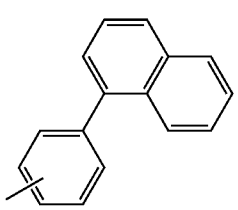

(23)
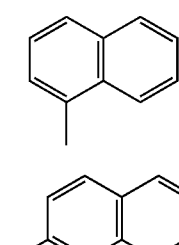

(24)
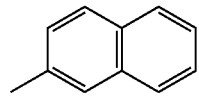

(25)
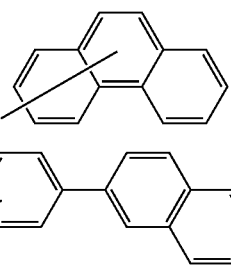

(26)
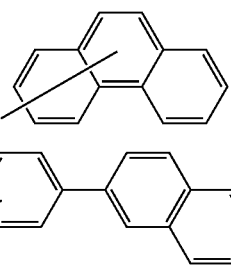

5. The material for an organic EL device of claim 1, wherein $R_1$ to $R_4$ are each independently at least one selected from hydrogen, deuterium, a phenyl group, a methyl group, fluorine, and a cyano group.

6. The material for an organic EL device of claim 3, wherein $L_1$ and/or $L_2$ are each independently an arylene group selected from Formulae (28) to (29):

(28)
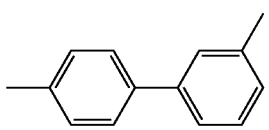

(29)
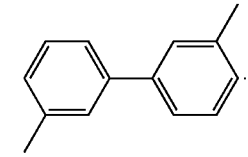

7. The material for an organic EL device of claim 1, having a molecular weight from about 500 g/mol to about 1,000 g/mol.
8. The material for an organic EL device of claim 1, wherein the material for an organic EL device is at least one selected from Formulae (30) to (43):
(30)
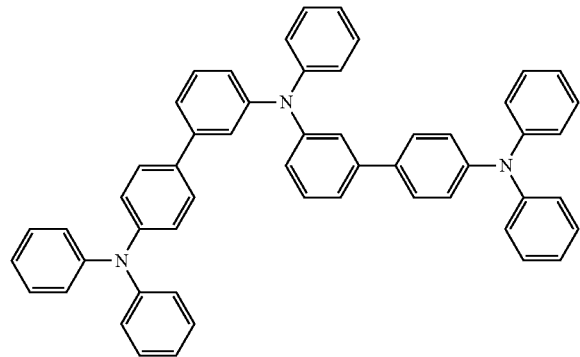
(31)
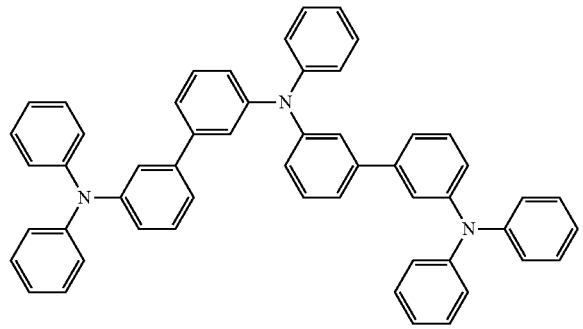
(32)
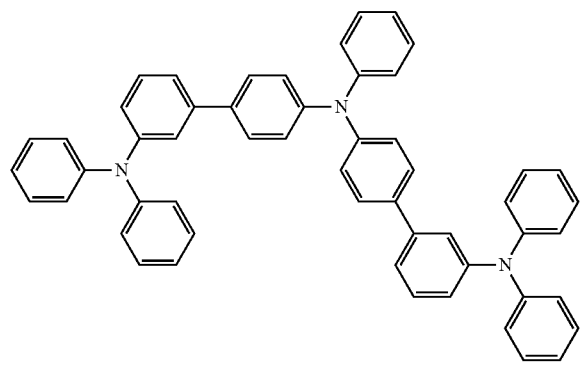
(33)
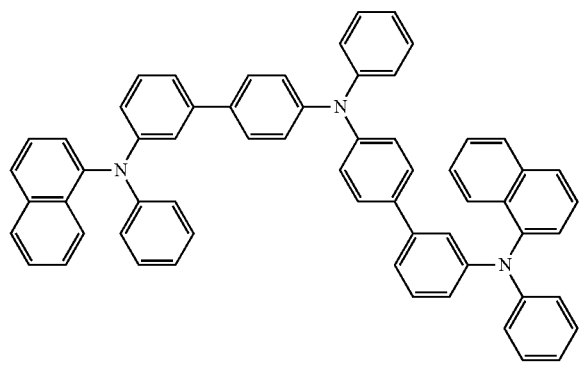
(34)
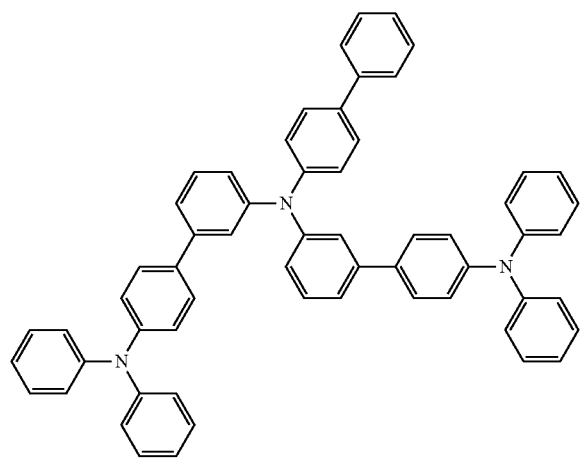
(35)
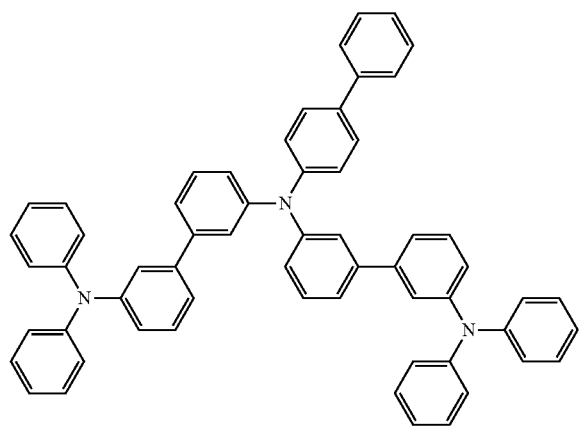

-continued
(36)
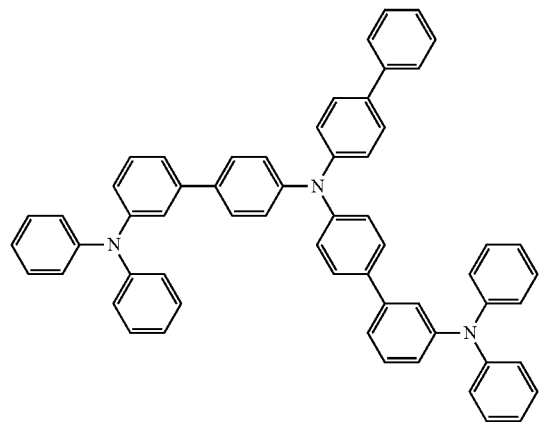
(37)
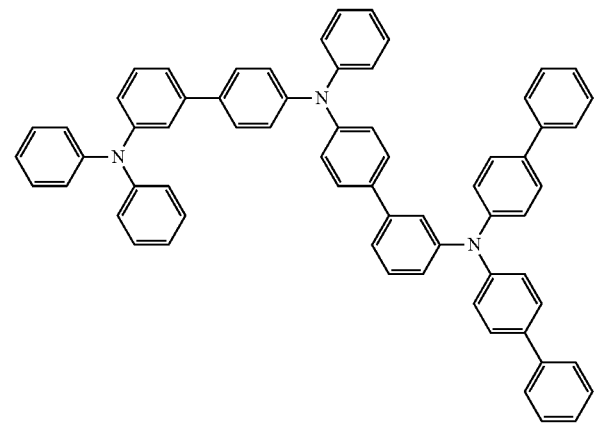
(38)
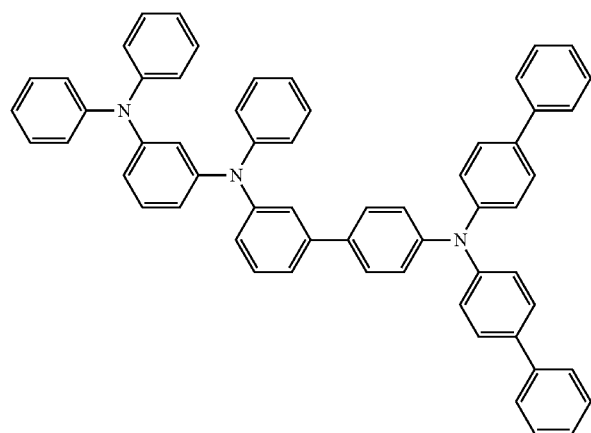
(39)
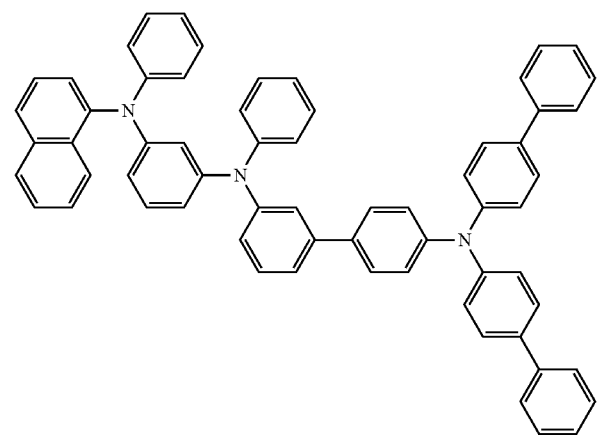
(40)
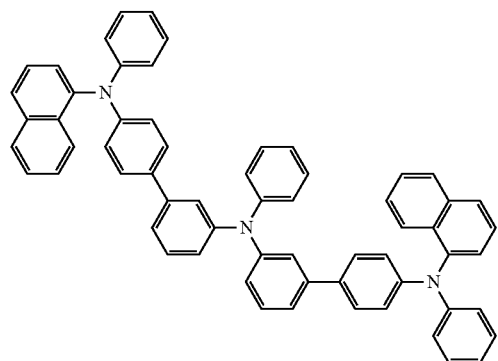
(41)
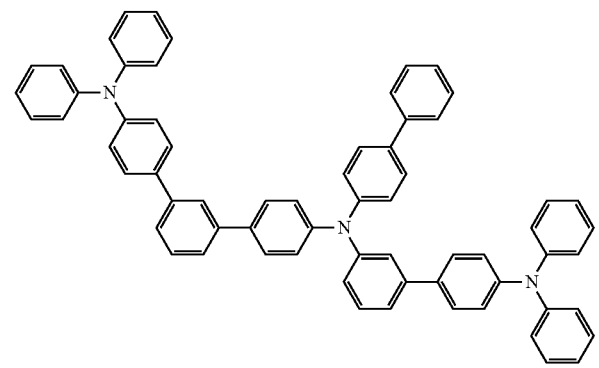

-continued (42)

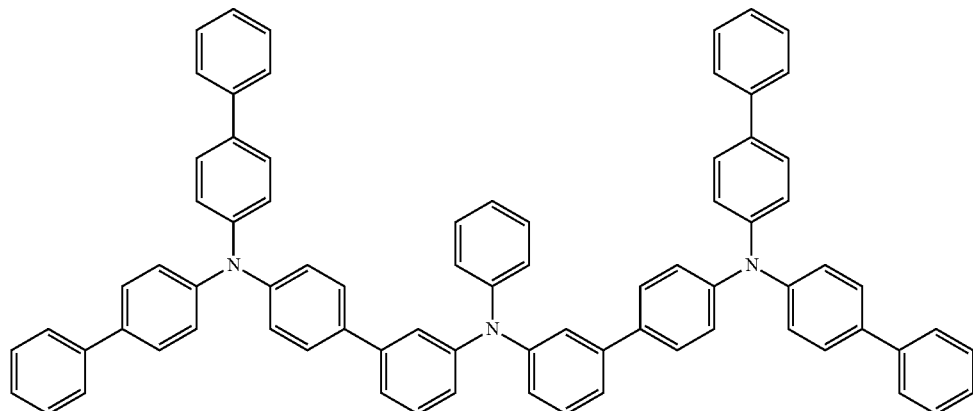

(43)

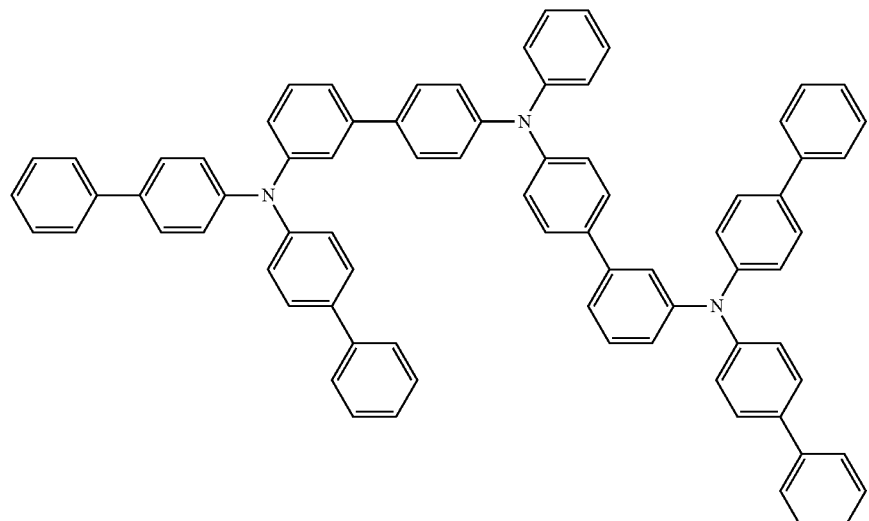

9. An organic electroluminescent (EL) device, comprising:
an anode;
a cathode facing the anode; and
a plurality of organic layers between the anode and the cathode,
wherein at least one selected from the plurality of organic layers comprises a material for an organic EL device, represented by Formula 1:

Formula 1

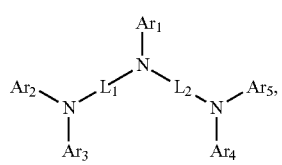

(1)

wherein in Formula 1, Formula 1 represents a triamine compound, and wherein Ar₁ to Ar₅ are each independently selected from a substituted or unsubstituted aryl group having 6 to 30 carbon atoms for forming a ring and a substituted or unsubstituted heteroaryl group having 4 to 30 carbon atoms for forming a ring, and L₁ and L₂ are each independently represented by Formula 2:

Formula 2

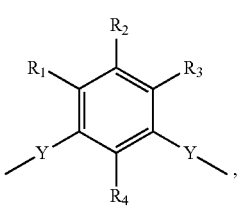

(2)

wherein Y is selected from a direct linkage and a substituted or unsubstituted arylene group having 6 to 30 carbon atoms for forming a ring, and
R₁ to R₄ are each independently selected from hydrogen, deuterium, a halogen atom, a hydroxyl group, a cyano group, a nitro group, an alkoxy group, an aryloxy group, an alkyl or aryl substituted silyl group, an alkyl or aryl substituted boryl group, a substituted or unsubstituted alkyl group, a substituted or unsubstituted aryl group, and a substituted or unsubstituted heteroaryl group.

10. The organic EL device of claim 9, wherein the plurality of organic layers comprise a hole injection layer, a hole transport layer, and an emission layer, and the material for an organic EL device is comprised in at least one layer selected from the hole injection layer, the hole transport layer, and the emission layer.

11. The organic EL device of claim 10, wherein the material for an organic EL device is comprised in a layer adjacent to the emission layer.

12. The organic EL device of claim 9, wherein $L_1$ and/or $L_2$ are each independently an arylene group selected from Formulae (3) to (14):

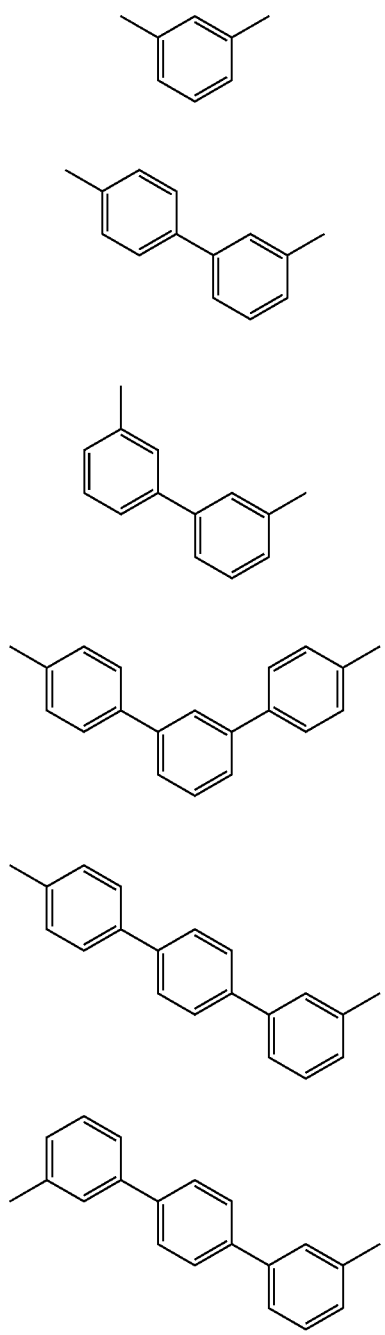

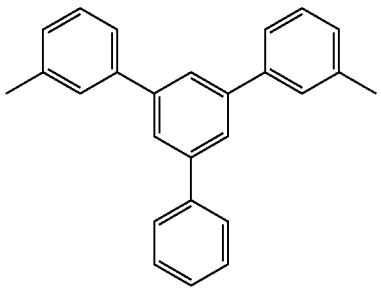

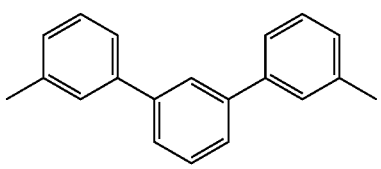

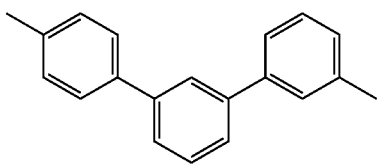

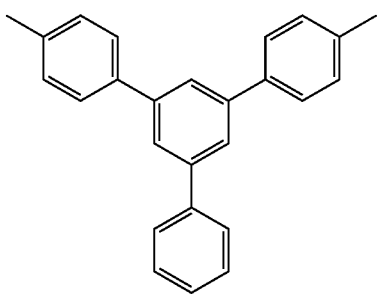

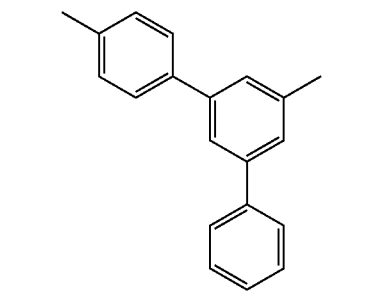

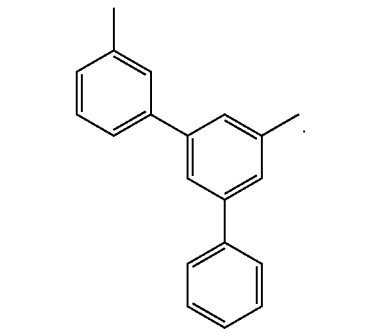

13. The organic EL device of claim 9, wherein the material for an organic EL device is at least one selected from Formulae (30) to (43):

(30)
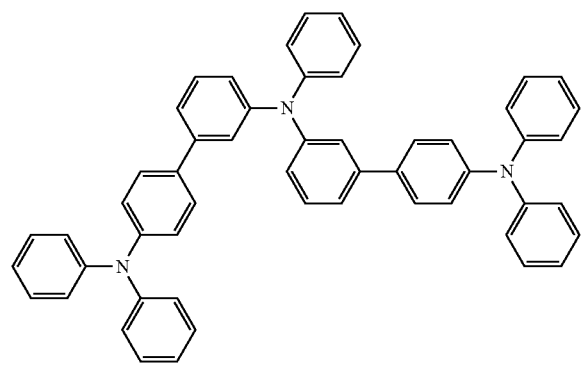
(31)
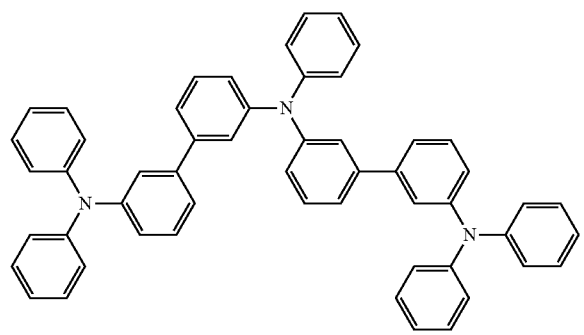
(32)
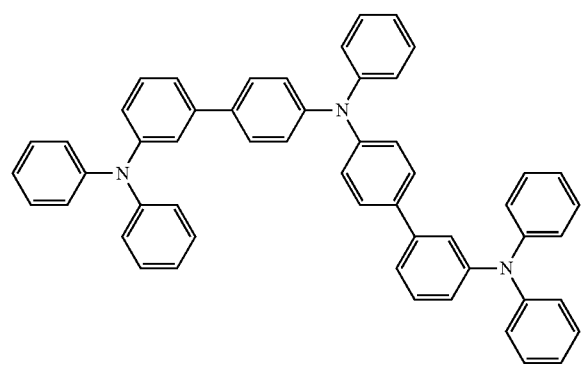
(33)
(34)
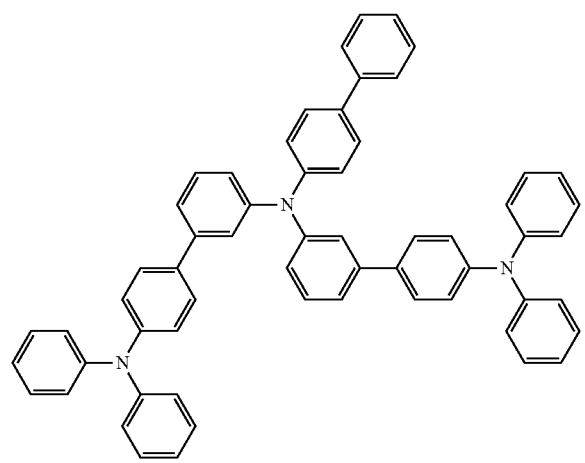
(35)
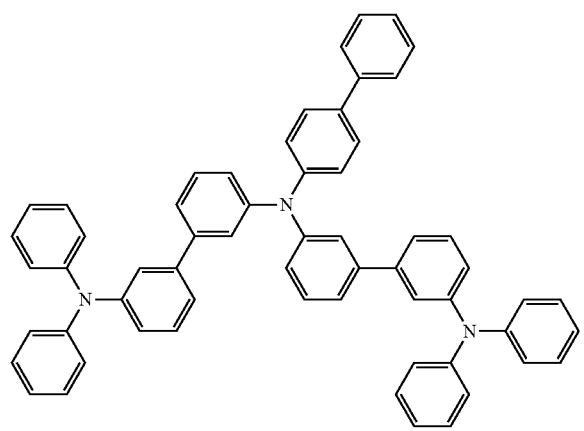

(36)
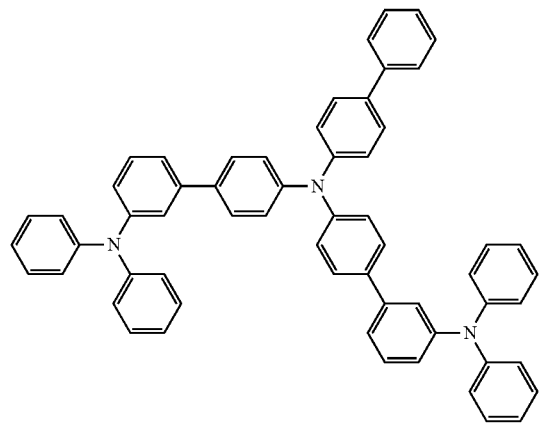
(37)
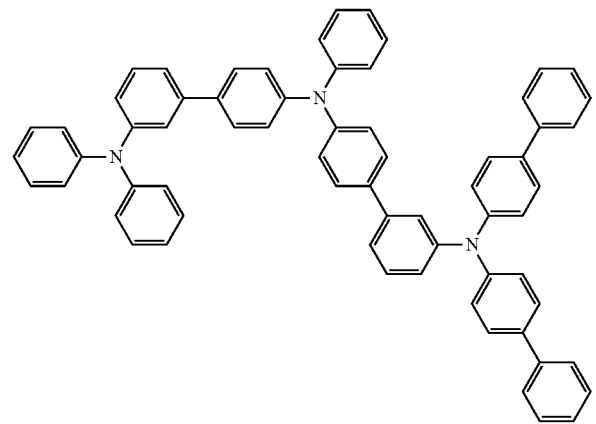
(38)
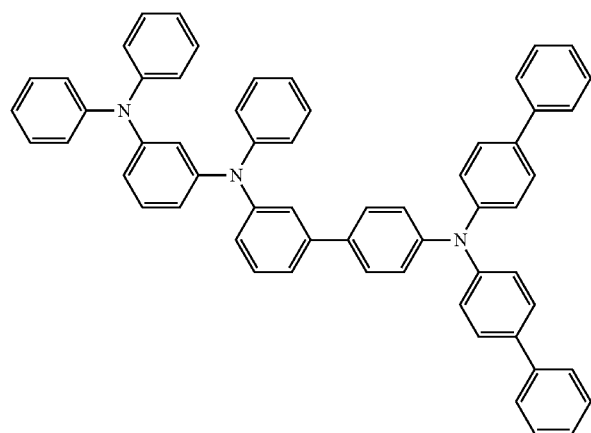
(39)
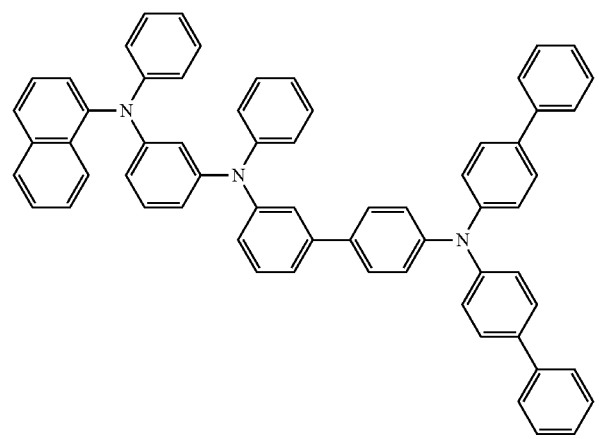
(40)
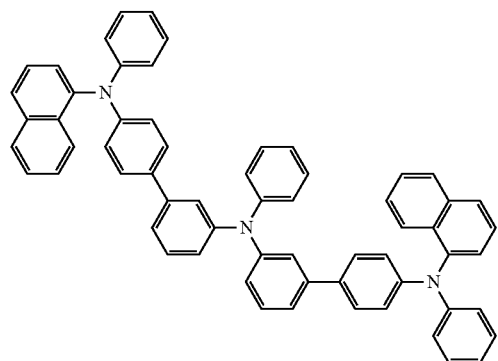
(41)
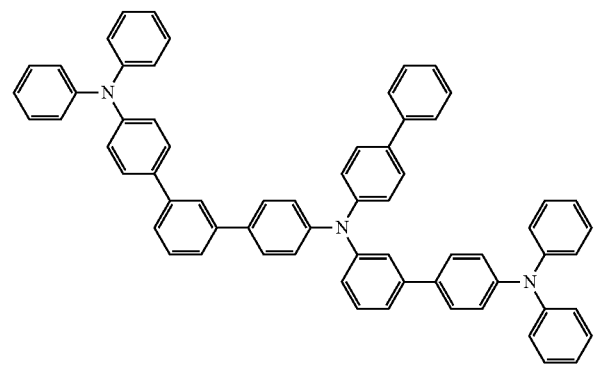

(42)
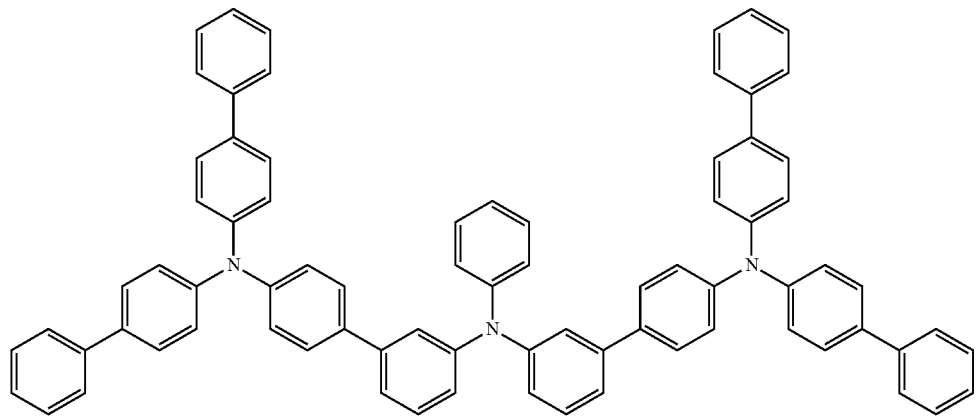
(43)
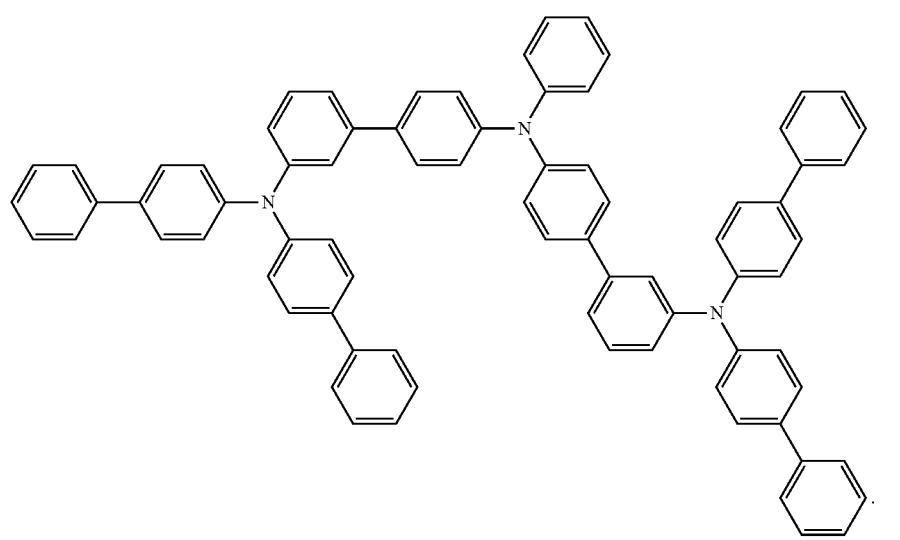
* * * * *